US009164044B2

(12) United States Patent
Hara et al.

(10) Patent No.: US 9,164,044 B2
(45) Date of Patent: Oct. 20, 2015

(54) CHARGED PARTICLE BEAM LITHOGRAPHY APPARATUS, INSPECTION APPARATUS AND INSPECTION METHOD OF PATTERN WRITING DATA

(71) Applicant: NuFlare Technology, Inc., Numazu-shi (JP)

(72) Inventors: Shigehiro Hara, Kanagawa (JP); Yasuo Kato, Kanagawa (JP); Akihito Anpo, Tokyo (JP); Noriaki Nakayamada, Kanagawa (JP)

(73) Assignee: NuFlare Technology, Inc., Namazu-shi (JP)

( * ) Notice: Subject to any disclaimer, the term of this patent is extended or adjusted under 35 U.S.C. 154(b) by 36 days.

(21) Appl. No.: 13/849,807

(22) Filed: Mar. 25, 2013

(65) Prior Publication Data

US 2013/0264478 A1 Oct. 10, 2013

(30) Foreign Application Priority Data

Mar. 29, 2012 (JP) ................. 2012-077844
Mar. 29, 2012 (JP) ................. 2012-077845

(51) Int. Cl.
*G01N 23/00* (2006.01)
*G01N 27/00* (2006.01)
*H01J 37/317* (2006.01)
*G03F 1/86* (2012.01)

(52) U.S. Cl.
CPC ............ *G01N 23/00* (2013.01); *G01N 27/00* (2013.01); *G03F 1/86* (2013.01); *H01J 37/3174* (2013.01); *H01J 2237/31769* (2013.01)

(58) Field of Classification Search
CPC ............................. G01N 23/00; H01J 37/3174

USPC ................................... 250/492.2, 492.3
See application file for complete search history.

(56) References Cited

U.S. PATENT DOCUMENTS

| 8,207,514 | B2 | 6/2012 | Hara et al. | |
|---|---|---|---|---|
| 2007/0194250 | A1* | 8/2007 | Suzuki et al. | 250/492.2 |
| 2010/0078556 | A1* | 4/2010 | Fujita et al. | 250/310 |
| 2011/0068281 | A1* | 3/2011 | Hara et al. | 250/492.22 |
| 2012/0085940 | A1 | 4/2012 | Matsumoto | |

FOREIGN PATENT DOCUMENTS

| JP | 2011-66264 | 3/2011 |
|---|---|---|
| JP | 2012-15244 | 1/2012 |
| JP | 2012-84659 | 4/2012 |

OTHER PUBLICATIONS

Office Action issued Sep. 25, 2014 in Korean Patent Application No. 10-2013-0034152 (with English language translation).

* cited by examiner

*Primary Examiner* — Nicole Ippolito
*Assistant Examiner* — Wyatt Stoffa
(74) *Attorney, Agent, or Firm* — Oblon, McClelland, Maier & Neustadt, L.L.P.

(57) ABSTRACT

An inspection method of pattern writing data includes creating an area map of a figure pattern written on a target object for each modulation rate for modulating a dose by using modulation rate data to modulate the dose in a case that a plurality of figure patterns is written on the target object by using a charged particle beam, and layout data in which the plurality of figure patterns is defined; converting the layout data into pattern writing data to be input into a lithography apparatus; and inspecting an amount of electric charge for each predetermined region by using the area map when a pattern is written on the target object by using the pattern writing data.

5 Claims, 24 Drawing Sheets

Table Of Relation Between Index Number Given To Figure And Dose

| Index Number | Dose Modulated Amount |
|---|---|
| 20 | 100% |
| 21 | 120% |
| 22 | 140% |

Mesh For Proximity Effect Correction

Map Of Index Number N

| $M^N_{(0,2)}$ | $M^N_{(1,2)}$ | $M^N_{(2,2)}$ |
|---|---|---|
| $M^N_{(0,1)}$ | $M^N_{(1,1)}$ | $M^N_{(2,1)}$ |
| $M^N_{(0,0)}$ | $M^N_{(1,0)}$ | $M^N_{(2,0)}$ |

FIG. 15

| Mesh ID | Index Number | | |
|---|---|---|---|
| | 20 | 21 | 22 |
| (0, 0) | | | |
| (1, 0) | | | |
| (2, 0) | | | |
| (0, 1) | | | |
| (1, 1) | | | |
| (2, 1) | | | |
| (0, 2) | | | |
| (1, 2) | | | |
| (2, 2) | | | |

FIG. 16

|  | Index Number | | | Skip Flag |
|---|---|---|---|---|
| Mesh ID | 20 | 21 | 22 | |
| (0, 0) | | | | 0 | Calculate For Inspection
| (1, 0) | | | | 1 | Skip Calculation
| (2, 0) | | | | 1 | For Inspection
| (0, 1) | | | | |
| (1, 1) | | | | |
| (2, 1) | | | | |
| (0, 2) | | | | |
| (1, 2) | | | | |
| (2, 2) | | | | |

FIG. 17

|  | Skip Pointer | Index Number | | |
|---|---|---|---|---|
| Mesh ID | | 20 | 21 | 22 |
| | $P_1$ | | | | ← First Pointer
| (0, 0) | | | | |
| (1, 0) | | | | |
| (2, 0) | | | | |
| (0, 1) | $P_2$ | | | |
| (1, 1) | | | | |
| (2, 1) | | | | |
| (0, 2) | $P_3$ | | | |
| (1, 2) | | | | |
| (2, 2) | | | | |

FIG. 18

Index Number

| 20 | 21 | 22 | |
|---|---|---|---|
|  |  |  | Value Corresponding To (0, 1) |
|  |  |  | Value Corresponding To (0, 2) |

FIG. 20

| Mesh ID | Index Number | | |
|---|---|---|---|
|  | 20 | 21 | 22 |
| (0, 1) |  |  |  |
| (0, 2) |  |  |  |

FIG. 21

CHARGED PARTICLE BEAM LITHOGRAPHY APPARATUS, INSPECTION APPARATUS AND INSPECTION METHOD OF PATTERN WRITING DATA

CROSS-REFERENCE TO RELATED APPLICATION

This application is based upon and claims the benefit of priority from prior Japanese Patent Application No. 2012-077844 filed on Mar. 29, 2012 in Japan, and prior Japanese Patent Application No. 2012-077845 filed on Mar. 29, 2012 in Japan, the entire contents of which are incorporated herein by reference.

BACKGROUND OF THE INVENTION

1. Field of the Invention

Embodiments described herein relate generally to a charged particle beam lithography apparatus, an inspection method, and an inspection apparatus of pattern writing data and, for example, relate to a technique of inspecting input data into a lithography apparatus for abnormalities 2. Related Art A lithography technique which leads development of micropatterning of a semiconductor device is a very important process for exclusively generating a pattern in semiconductor manufacturing processes. In recent years, with an increase in integration density of an LSI, a circuit line width required for semiconductor devices is getting smaller year by year. In order to form a desired circuit pattern on such semiconductor devices, a high-precision original pattern (also called a reticle or a mask) is needed. In this case, an electron beam pattern writing technique has an essentially excellent resolution, and is used in production of precise original patterns.

FIG. 28 is a conceptual diagram for explaining an operation of a variable-shaped electron beam lithography apparatus. The variable-shaped electron beam (EB: Electron Beam) lithography apparatus operates as described below. A rectangular opening 411 to form an electron beam 330 is formed in a first aperture plate 410. A variable-shaped opening 421 to shape the electron beam 330 having passed through the opening 411 of the first aperture plate 410 into a desired oblong shape is formed in a second aperture plate 420. The electron beam 330 shone from a charged particle source 430 and having passed through the opening 411 of the first aperture plate 410 is deflected by a deflector and passes through a portion of the variable-shaped opening 421 of the second aperture plate 420 before being shone on a target object 340 placed on a stage continuously moving in a predetermined direction (for example, the X direction). That is, a rectangular shape capable of passing through both the opening 411 of the first aperture plate 410 and the variable-shaped opening 421 of the second aperture plate 420 is written in a pattern writing region of the target object 340 placed on the stage continuously moving in the X direction. The method of forming any shape by causing a beam to pass through both the opening 411 of the first aperture plate 410 and the variable-shaped opening 421 of the second aperture plate 420 is called the variable-shaped beam method (VSB method).

In electron beam pattern writing, dimensional variations caused by mask processes or an unknown mechanism are resolved by adjusting a dose of an electron beam. Conventionally, a correction model is set and an operation to correct the dose based on the model is performed inside the lithography apparatus and the dose is controlled in accordance with the operation result inside the lithography apparatus. For example, the proximity effect correction operation can be cited. However, even if the dose calculated inside the lithography apparatus is used, a correction residual may remain. Particularly, there is a case when the dose should be additionally controlled for a partial pattern or a local region, separately from other patterns or regions. In such a case, the modulated dose needs to be set by a user or correction tool or the like before data is input into the lithography apparatus. However, if the value set by the user or an operation result by the correction tool is incorrect, such a value is input into the lithography apparatus and the value is used by the lithography apparatus, causing a problem of irradiation of a beam of an abnormal dose. The beam irradiation of such an abnormal dose causes abnormalities of pattern dimensions CD. Further, if the dose is an extremely abnormal value, resist evaporation and by extension, lithography apparatus contamination (or a lithography apparatus failure) could be caused by such evaporation.

BRIEF SUMMARY OF THE INVENTION

In accordance with one aspect of the present invention, an inspection method of pattern writing data includes creating an area map of a figure pattern written on a target object for each modulation rate for modulating a dose by using modulation rate data to modulate the dose in a case that a plurality of figure patterns is written on the target object by using a charged particle beam, and layout data in which the plurality of figure patterns is defined; converting the layout data into pattern writing data to be input into a lithography apparatus; and inspecting an amount of electric charge for each predetermined region by using the area map when a pattern is written on the target object by using the pattern writing data.

In accordance with another aspect of the present invention, an inspection apparatus of pattern writing data includes a data storage unit configured to store an area map of a figure written on a target object created by using modulation rate data to modulate a dose when a plurality of the figure patterns is written on the target object by using a charged particle beam, and layout data in which the plurality of figure patterns is defined and an inspection unit configured to inspect an amount of electric charge for each predetermined region when a pattern is written on the target object by using the area map.

In accordance with further another aspect of the present invention, a charged particle beam lithography apparatus includes a data storage unit configured to store an electric charge amount map defining an amount of electric charge of an irradiated charged particle beam for each mesh region of a plurality of mesh regions obtained by dividing a pattern writing region of a target object into mesh shapes, the electric charge amount map being input from outside; a charge amount inspection unit configured to inspect whether the amount of electric charge defined in the electric charge amount map is equal to or less than a threshold in each mesh region; and a writing unit configured to write a pattern on the target object by using a charged particle beam based on pattern writing data paired with the electric charge amount map.

In accordance with further another aspect of the present invention, an inspection apparatus in another aspect of the present invention includes a data storage unit configured to store an electric charge amount map defining an amount of electric charge of an irradiated charged particle beam and input from outside for each mesh region obtained by dividing a pattern writing region of a target object into mesh shapes and a charge amount inspection unit configured to inspect whether the amount of electric charge defined in the electric charge amount map is equal to or less than a threshold in each mesh region.

In accordance with further another aspect of the present invention, an inspection method of pattern writing data includes converting layout data in which a plurality of figure patterns is defined into pattern writing data to be input into a lithography apparatus; creating an electric charge amount map defining an amount of electric charge of an irradiated charged particle beam for each mesh region of a plurality of mesh regions, obtained by dividing a pattern writing region of a target object into mesh shapes, in parallel with the converting; and inspecting whether an amount of electric charge defined in the electric charge amount map is equal to or less than a threshold for each mesh region.

BRIEF DESCRIPTION OF THE DRAWINGS

FIG. 7 is a conceptual diagram showing the configuration of a pattern writing system when an inspection method of pattern writing data in Embodiment 1 is focused on;

FIG. 8 is a conceptual diagram showing another example of the configuration of the pattern writing system when the inspection method of pattern writing data in Embodiment 1 is focused on;

FIG. 15 is a diagram showing an example of an area map in Embodiments 1 to 3;

FIG. 16 is a diagram showing an example of a data structure of the area map in Embodiments 1 to 3;

FIG. 17 is a diagram showing another example of the data structure of the area map in Embodiments 1 to 3;

FIG. 18 is a diagram showing still another example of the data structure of the area map in Embodiments 1 to 3;

FIG. 20 is a diagram showing still another example of the data structure of the area map in Embodiments 1 to 3;

FIG. 21 is a diagram showing still another example of the data structure of the area map in Embodiments 1 to 3;

DETAILED DESCRIPTION OF THE INVENTION

In the following embodiments, an inspection method and apparatus capable of avoiding beam irradiation of an abnormal dose due to pattern writing data input into a lithography apparatus will be described.

Also in the following embodiments, a configuration using an electron beam as an example of a charged particle beam will be described. However, the charged particle beam is not limited to an electron beam, and a beam such as an ion beam using charged particles may also be used. Also, a variable-shaped lithography apparatus will be described as an example of a charged particle beam apparatus.

Embodiment 1

Figure 1:
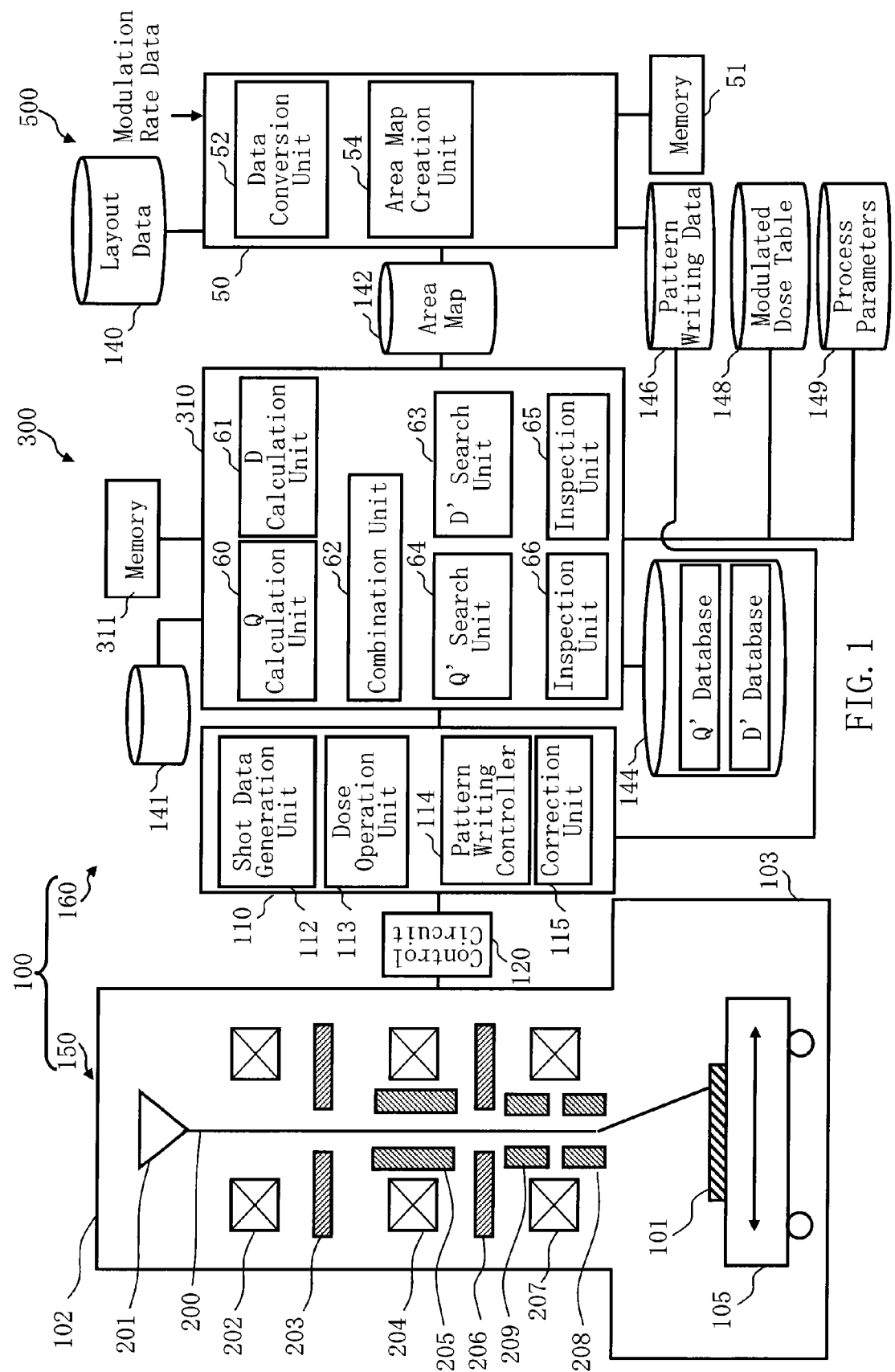
FIG. 1 is a conceptual diagram showing the configuration of a pattern writing system according to Embodiment 1.

FIG. 1 is a conceptual diagram showing the configuration of a pattern writing system according to Embodiment 1. In FIG. 1, the pattern writing system includes a lithography apparatus 100, an inspection apparatus 300, and a pattern writing data conversion apparatus 500. In addition, a modulated dose table creation tool, a parameter information creation tool and the like may also be included.

The lithography apparatus (or "writing apparatus") 100 includes a pattern generator (or "writing unit") 150 and a controller 160. The lithography apparatus 100 is an example of a charged particle beam lithography apparatus. Particularly, the lithography apparatus 100 is an example of a variable-shaped lithography apparatus. The pattern generator 150 includes an electron lens barrel 102 and a pattern writing chamber 103. In the electron lens barrel 102, an electron gun assembly 201, an illumination lens 202, a first aperture plate 203, a projection lens 204, a deflector 205, a second aperture plate 206, an objective lens 207, a main deflector 208, and a sub-deflector 209. An XY stage 105 is arranged inside the pattern writing chamber 103. A target object 101 such as a mask on which a pattern should be written is arranged on the XY stage 105 while a pattern is written. The target object 101 includes an exposure mask used for fabricating a semiconductor device. The target object 101 also includes mask blanks to which a resist is coated and on which no pattern is written.

The controller 160 includes a control computer 110 and a control circuit 120. The control computer 110 and the control circuit 120 are connected via a bus (not shown). A shot data generation unit 112, a dose operation unit 113, a pattern writing controller 114, and a correction unit 115 are arranged inside the control computer 110. The function such as the shot data generation unit 112, the dose operation unit 113, the pattern writing controller 114, and the correction unit 115 may be configured by hardware such as an electric circuit or by software such as a program executing these functions. Alternatively, the function may be configured by a combination of hardware and software. Information input into or output from the shot data generation unit 112, the dose operation unit 113, the pattern writing controller 114, or the correction unit 115 and information during operation are stored in a memory (not shown) each time.

The pattern writing data inspection apparatus 300 includes a control computer 310, a memory 311, and storage apparatuses 141, 142, 144 such as magnetic disk drives. The control computer 310, the memory 311, and the storage apparatuses 141, 142, 144 are mutually connected via a bus (not shown). A charge amount Q calculation unit 60, a maximum dose Dmax calculation unit 61, a combination unit 62, a charge amount threshold Q' search unit 64, a dose threshold D' search unit 63, and inspection units 65, 66 are arranged inside the control computer 310. The function such as the charge amount Q calculation unit 60, the maximum dose Dmax calculation unit 61, the combination unit 62, the charge amount threshold Q' search unit 64, the dose threshold D' search unit 63, and the inspection units 65, 66 may be configured by hardware such as an electric circuit or by software such as a program executing these functions. Alternatively, the function may be configured by a combination of hardware and software. Information input into or output from the charge amount Q calculation unit 60, the maximum dose Dmax calculation unit 61, the combination unit 62, the charge amount threshold Q' search unit 64, the dose threshold D' search unit 63, or the inspection units 65, 66 and information during operation are stored in the memory 311 each time. A charge amount threshold Q' database that can be searched for a charge amount threshold Q' indicating the maximum amount of electric charge available for process parameters and lithography apparatus specifications is stored in the storage apparatus 144. Further, a dose threshold D' database that can be searched for a dose threshold D' indicating the maximum dose available for process parameters and lithography apparatus specifications is stored in the storage apparatus 144.

The pattern writing data conversion apparatus 500 includes a control computer 50, a memory 51, and storage apparatuses 140, 148 such as magnetic disk drives. The control computer 50, the memory 51, and the storage apparatuses 140, 148 are mutually connected via a bus (not shown). A data conversion unit 52 and an area map creation unit 54 are arranged inside the control computer 50. The function such as the data conversion unit 52 and the area map creation unit 54 may be configured by hardware such as an electric circuit or by software such as a program executing these functions. Alternatively, the function may be configured by a combination of hardware and software. Information input into or output from the data conversion unit 52 or the area map creation unit 54 and information during operation are stored in the memory 51 each time. In addition, layout data (for example, CAD data) as design data created by the user is stored in the storage apparatus 140.

The control computer 110 of the lithography apparatus 100 is connected to the pattern writing data inspection apparatus 300, the pattern writing data conversion apparatus 500, and the other storage apparatuses 148, 149 such as magnetic disk drives via a network (not shown). A modulated dose table described later is stored in the storage apparatus 148. Process parameters used when target layout data is written are stored in the storage apparatus 149. As process parameters, for example, the resist to be used or the like is defined.

Here, in FIG. 1, only the configuration needed to describe Embodiment 1 is shown. The lithography apparatus 100, the pattern writing data inspection apparatus 300, and the pattern writing data conversion apparatus 500 may normally include other necessary configurations. For example, a multi-stage deflector of the 2-stage main/sub-deflectors, the main deflector 208 and the sub-deflector 209, is used for position deflection, but a 1-stage deflector or a multi-stage deflector of three stages or more may be used for position deflection. In addition, an input apparatus such as a mouse or keyboard, a monitor apparatus, or an external interface circuit may be connected to the lithography apparatus 100, the pattern writing data inspection apparatus 300, and the pattern writing data conversion apparatus 500.

It is necessary to convert layout data into pattern writing data that can be input into the lithography apparatus 100 to perform a pattern writing process in the lithography apparatus 100. Though not illustrated, the lithography apparatus 100 internally carries out a calculation of a dose correction such as a proximity effect correction, but a correction residual may still remain even if the dose calculated in the lithography apparatus is used. Thus, the user may particularly wish to additionally control the dose for a partial pattern or a local region, separately from other patterns or regions. In such a case, the modulated dose is set by the user or the correction tool or the like before data is input into the lithography apparatus.

Figures 2, 3:
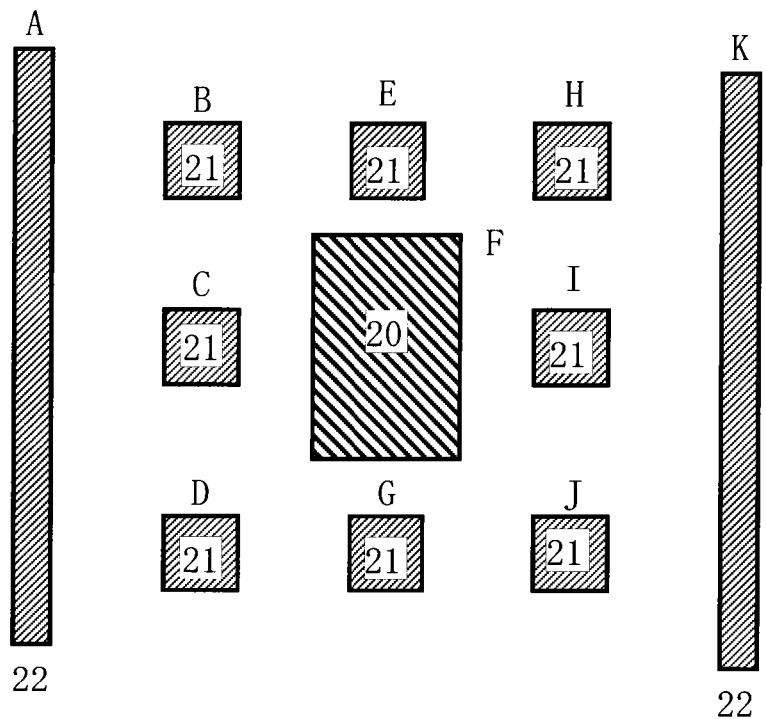
FIG. 2 is a diagram showing an example of a figure in Embodiment 1.
FIG. 3 is a diagram showing an example of a modulated dose table in Embodiment 1.

FIG. 2 is a diagram showing an example of a figure (figure pattern) in Embodiment 1. In FIG. 2, for example, a plurality of figures (figure patterns) A to K is arranged in layout data. Then, there may be a case when the figures A, K, the figures B to E, G to J, and the figure F should be written by using different doses. Thus, the modulated dose rate for the figures A, K, the modulated dose rate for the figures B to E, G to J, and the modulated dose rate for the figure F are preset. The dose after the modulation is calculated, for example, as a value obtained by multiplying a dose d after proximity effect corrections and the like being calculated inside the lithography apparatus 100 by the modulated dose rate. Therefore, the following modulated dose table is created.

FIG. 3 is a diagram showing an example of a modulated dose table in Embodiment 1. As shown in FIG. 2, an index number (identifier) is attached to each of a plurality of figures in the layout data. Then, as shown in FIG. 3, the modulated dose table has the modulated dose rate defined as a dose modulated amount for each index number. In FIG. 3, the modulated dose rate for the figure of the index number 20 is defined as 100%. The modulated dose rate for the figure of the index number 21 is defined as 120%. The modulated dose rate for the figure of the index number 22 is defined as 140%. Such a modulated dose table is created by a modulated dose table creation tool (not shown). The modulated dose table creation tool may create associated data after modulation rate data of the modulated dose rates set by the user or the correction tool or the like and the index numbers of respective corresponding figures being input.

Figure 4:
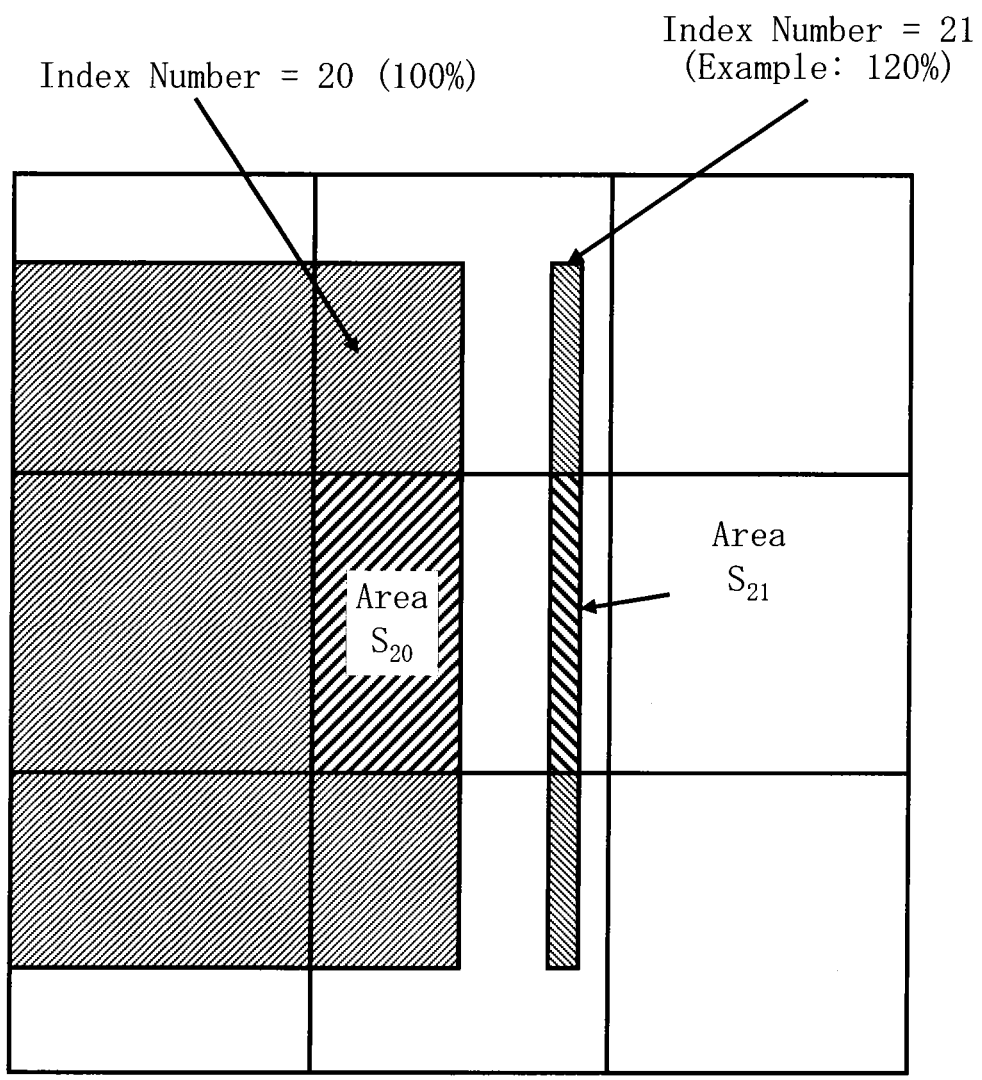
FIG. 4 is a conceptual diagram for explaining an amount of electric charge in Embodiment 1.

FIG. 4 is a conceptual diagram for explaining the amount of electric charge in Embodiment 1. As shown in FIG. 4, a pattern writing region is divided into mesh regions in a mesh shape of a predetermined size and, for example, a proximity effect correction calculation is carried out for each mesh region. However, a case when a portion of the figure of the index number 20 and a portion of the figure of the index number 21 are mixed in the same mesh region arises. In such a case, if the mesh region is irradiated with a unique dose corrected by a proximity effect correction calculation, as described above, a correction residual remains. Thus, in Embodiment 1, when the figure of the index number 20 in the mesh region is written, the mesh region is irradiated with the dose of a value obtained by multiplying a dose d20 for the figure of the index number 20 by the modulated dose rate (100%) of the index number 20. On the other hand, when the figure of the index number 21 in the same mesh region is written, the mesh region is irradiated with the dose of a value obtained by multiplying a dose d21 for the figure of the index number 21 by the modulated dose rate (120%) of the index number 21. Thus, the total amount of electric charge of the amount of electric charge of the figure area S20 of the index number 20 in the mesh region×dose d20×modulated dose rate (100%) and the amount of electric charge of the figure area S21 of the index number 21×dose d21×modulated dose rate (120%) is stored in the mesh region. If the modulated dose rate set by the user or the modulated dose rate in an operation result of the correction tool or the like is incorrect, when such a value is input into the lithography apparatus and the value is used by the lithography apparatus unchanged, a beam of an abnormal dose will be shone. Beam irradiation of such an abnormal dose causes storage of an abnormal amount of electric charge in the mesh regions. Accordingly, abnormalities of the pattern dimensions CD are caused. Further, if the dose is an extremely abnormal value, resist evaporation and by extension, lithography apparatus contamination (or a lithography apparatus failure) could be caused by such evaporation. Thus, in Embodiment 1, the amount of electric charge is inspected for abnormalities before the data conversion process is performed in the lithography apparatus 100 or before the data conversion process is completed. Similarly, whether the irradiated maximum dose itself is an abnormal value is inspected.

Figure 5:
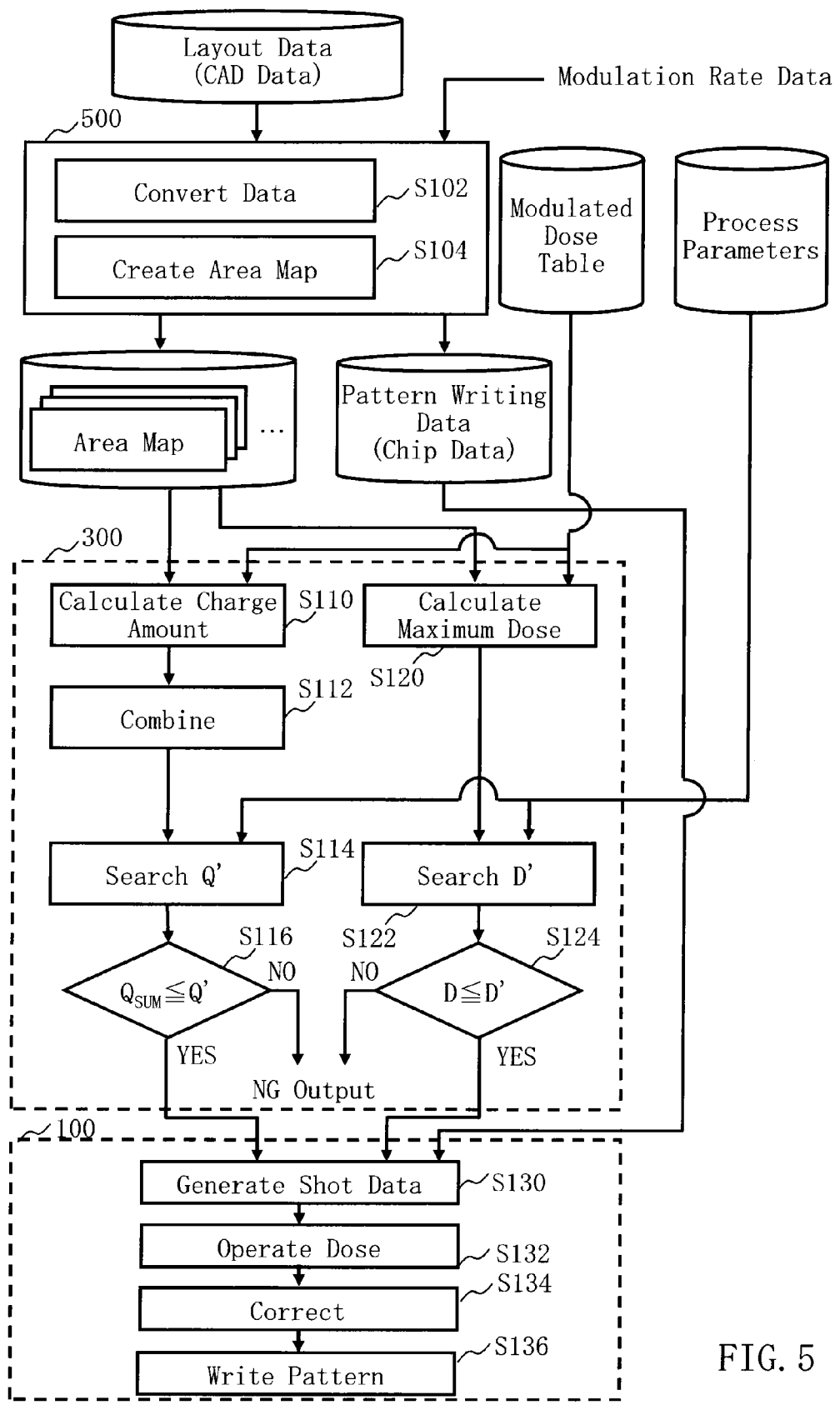
FIG. 5 is a flow chart showing principal processes from data conversion of pattern writing data to a pattern writing process in Embodiment 1.

FIG. 5 is a flow chart showing principal processes from data conversion of pattern writing data to a pattern writing process in Embodiment 1. As shown in FIG. 5, a data conversion process (S102) and an area map creation process (S104) are performed by the pattern writing data conversion apparatus 500. Next, a series of processes including a charge amount Q calculation process (S110), a combination process (S112), a threshold Q' search process (S114), an inspection process (S116), a maximum dose Dmax calculation process (S120), a threshold D' search process (S122), and an inspection process (S124) are performed by the pattern writing data inspection apparatus 300. Then, a shot data generation process (S130), a dose operation process (S132), a correction process (S134), and a pattern writing process (S136) are performed by the lithography apparatus 100.

First, as the data conversion process (S102), the data conversion unit 52 reads layout data in which a plurality of figures is defined from the storage apparatus 140 and converts the data into pattern writing data in a format that can be input into the lithography apparatus 100. The generated pattern writing data is output and stored in the storage apparatus 146.

In the generated pattern writing data, as shown in FIG. 2, the index number (identifier) to identify the modulated dose rate (modulation rate) is attached to each figure as additional data. Alternatively, figures for which the modulated dose rate is defined and figures for which no modulated dose rate is defined may be mixed. In the case in which both types of figures are mixed, a predetermined modulated dose rate is used for figures for which no modulated dose rate is defined. For example, the modulated dose rate of 100% may be used.

A plurality of chips may be arranged in the one target object 101. Thus, layout data contains a plurality of pieces of chip data. For this case, the modulated dose rate may suitably be set for each chip. In such a case, the index number (identifier) to identify the modulated dose rate (modulation rate) is attached to each chip as additional data in the generated pattern writing data. Also in such a case, chips for which the modulated dose rate is defined and chips for which no modulated dose rate is defined may be mixed. In the case in which both types of chips are mixed, a predetermined modulated dose rate is used for chips for which no modulated dose rate is defined. For example, the modulated dose rate of 100% may be used. Alternatively, the index number may naturally be defined for each figure constituting a chip as additional data.

As the area map creation process (S104), the area map creation unit 54 creates an area map of figures written on the target object for each modulation rate that modulates the dose by using modulation rate data to modulate the dose when a plurality of figures is written on the target object by using an electron beam 200 and layout data. As the modulation rate data, a value set by the user or the correction tool or the like may be input. Each generated area map is output and stored in the storage apparatus 142. When a plurality of chips is arranged, the plurality of chips may be merged to create an area map of figures to be written on the target object for each modulation rate in a state in which figures of a plurality of modulated dose rates are mixed. When mutually different modulation rates are set to all chips, an area map may be created for each chip. When the same modulation rate is set to some chips, the chips of the same modulation rate may be merged to create an area map for each modulation rate.

The data conversion process (S102) and the area map creation process (S104) are suitably performed in parallel. Generally, the conversion process from layout data into pattern writing data needs a few tens of hours. For example, about 20 hours are needed. Then, a few hours, for example, about five hours are needed for the area map creation. Thus, by performing the data conversion process (S102) and the area map creation process (S104) in parallel, the area map creation time can be overlaid on the data conversion process time from layout data into pattern writing data. That is, the area map creation time does not have to be added to the conventional pattern writing work time.

Figure 6:
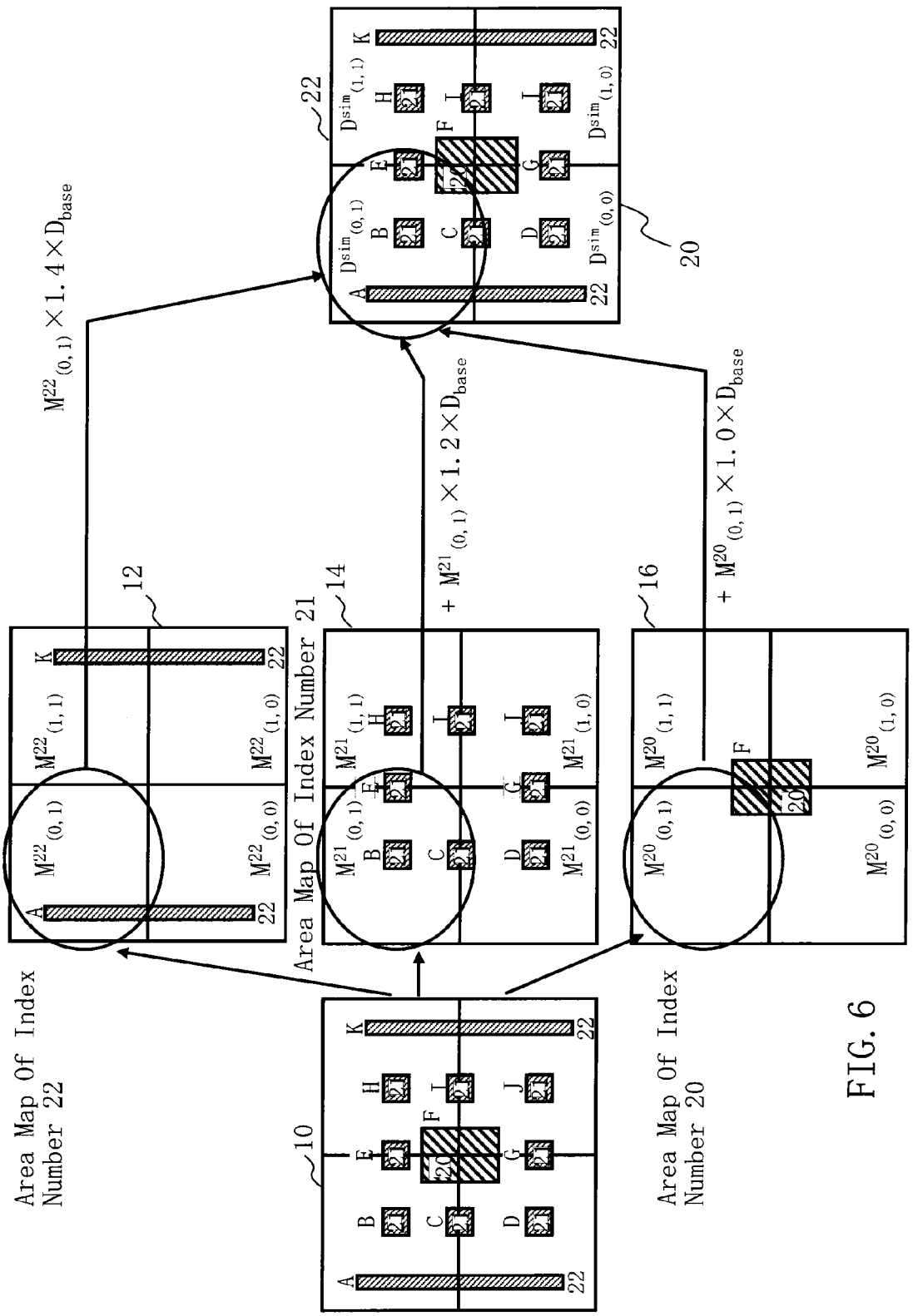
FIG. 6 is a conceptual diagram showing the flow of calculating the amount of electric charge in Embodiment 1.

FIG. 6 is a conceptual diagram showing the flow of calculating the amount of electric charge in Embodiment 1. In FIG. 6, layout data 10 is divided into mesh regions of a predetermined size. Then, an area map in which areas of figures in each mesh region are calculated is created for each index number. In the example of FIG. 6, an area map 12 collecting figures of the index number 22 is created. Similarly, an area map 14 collecting figures of the index number 21 is created. Similarly, an area map 16 collecting figures of the index number 20 is created. Each area map naturally becomes a map for each modulation rate.

Next, as the charge amount Q calculation process (S110), the charge amount Q calculation unit 60 reads each area map from the storage apparatus 142 and reads the modulated dose table from the storage apparatus 148 to calculate an amount of electric charge $Q_{(i,j)}$ obtained by multiplying an area value $M_{(i,j)}$ in the mesh region of coordinates (i, j), a modulated dose $R_N$ indicated by the index number N, and the base doses of the beam Dbase together for each mesh region of each area map. In other words, the amount of electric charge $Q_{(i,j)}$ for each mesh region of coordinates (i, j) of the area map of the index number N is defined by Formula (1) below by using the area $M_{N(i,j)}$ in the mesh region, the modulated dose rate Rk indicated by the index number N, and the base doses of the beam Dbase:

$$Q(i,j)=M_N(i,j) \cdot R_N D\text{base} \quad (1)$$

Each calculated amount of electric charge $Q_{(i,j)}$ is stored in the storage apparatus 141. The base doses of the beam Dbase may be preset.

As the combination process (S112), the combination unit 62 combines the same mesh regions of the area maps 12, 14, 16 to create a combined map 20. The combination unit 62 adds up the amounts of electric charge $Q_{(i,j)}$ of the same mesh regions to calculate a total amount of electric charge $Qsum_{(i,j)}$. Accordingly, an amount of electric charge Qsum stored due to the electron beam 200 with which each mesh region is irradiated can be determined. As each mesh value of the combined map 20, each corresponding amount of electric charge $Qsum_{(i,j)}$ is defined.

As the threshold Q' search process (S114), the charge amount threshold Q' search unit 64 reads process parameters from the storage apparatus 149 storing process parameters and reads apparatus specifications from the lithography apparatus 100 to search for a charge amount threshold Q' indicating the maximum amount of electric charge that can be used for such process parameters and apparatus specifications by referring to the charge amount threshold Q' database stored in the storage apparatus 144. The maximum amount of electric charge that can be used changes depending on apparatus specifications of the lithography apparatus 100. Apparatus specifications may be different depending on the lithography apparatus to be used. For example, apparatus specifications are different from model to model. Variations of the maximum amount of electric charge that can be used may be present even for the same model. Similarly, the maximum amount of electric charge that can be used is different depending on process parameters, for example, the resist type. Thus, the charge amount threshold Q' search unit 64 uses information (for example, search keywords) of these process parameters and apparatus specifications to search for the charge amount threshold Q' indicating the maximum amount of electric charge that can be used.

As the inspection process (S116), the inspection unit 66 inspects (judges) whether the amount of electric charge $Qsum_{(i,j)}$ for each combined mesh region is equal to or less than the charge amount threshold Q'. If, as a result of the inspection, the amount of electric charge $Qsum_{(i,j)}$ is larger than the charge amount threshold Q' in one of the mesh regions, error information is output as rejected pattern writing. If the amount of electric charge Qsum is equal to or less than the charge amount threshold Q' in all mesh regions, the lithography apparatus 100 is assumed to be able to perform a pattern writing process and OK information may be output to the pattern writing controller 114. In this manner, the inspection unit 66 inspects the amount of electric charge $sum_{(i,j)}$ of each mesh region (predetermined region) when a pattern is written on a target object by using an area map.

As the maximum dose Dmax calculation process (S120), the maximum dose Dmax calculation unit 61 reads the modulated dose table from the storage apparatus 148 to calculate the maximum dose Dmax. The maximum dose Dmax can be calculated by, for example, multiplying the maximum modulated dose rate among modulated dose rates indicated by a plurality of index numbers by the base doses of the beam Dbase. In the example of FIG. 3, for example, 140% is the maximum modulated dose rate and thus, the maximum dose Dmax can be determined by multiplying the value (140%) by the base doses of the beam Dbase.

As the threshold D' search process (S122), the dose threshold D' search unit 63 reads process parameters from the storage apparatus 149 storing process parameters and reads apparatus specifications from the lithography apparatus 100 to search for a dose threshold D' indicating the maximum dose that can be used for such process parameters and apparatus specifications by referring to the dose threshold D' database stored in the storage apparatus 144. The maximum dose that can be used changes depending on apparatus specifications of the lithography apparatus 100. Apparatus specifications may be different depending on the lithography apparatus to be used. For example, apparatus specifications are different from model to model. Variations of the maximum dose that can be used may be present even for the same model. Similarly, the maximum dose that can be used is different depending on process parameters, for example, the resist type. Thus, the dose threshold D' search unit 63 uses information (for example, search keywords) of these process parameters and apparatus specifications to search for the dose threshold D' indicating the maximum dose that can be used.

As the inspection process (S124), the inspection unit 65 inspects (judges) whether the operated maximum dose threshold Dmax is equal to or less than the dose threshold D'. If, as a result of the inspection, the maximum dose Dmax is larger than the dose threshold D', error information is output as rejected pattern writing. If the maximum dose Dmax is equal to or less than the dose threshold D', the lithography apparatus 100 is assumed to be able to perform a pattern writing process and OK information may be output to the pattern writing controller 114.

Pattern writing data can be inspected for abnormalities by the above inspection process before the data conversion process of the pattern writing data in the lithography apparatus 100. Accordingly, useless work time in the lithography apparatus 100 can subsequently be avoided. The process in the inspection apparatus 300 can be completed in a few minutes. Therefore, pattern writing data can be inspected for abnormalities in an early stage. If an area map is created by the inspection apparatus 300, the area map creation time is further added and the inspection time increases for the added time. In Embodiment 1, by contrast, an area map is created in parallel at the same time as the generation of pattern writing data by, instead of the inspection apparatus 300, the pattern writing data conversion apparatus 500 upstream thereof and thus, only a few minutes by the inspection apparatus 300 are needed for the inspection of pattern writing data. Then, after the pattern writing data is inspected with no abnormality found, the pattern writing process is performed by the lithography apparatus 100.

As the shot data generation process (S130), the shot data generation unit 112 reads pattern writing data from the storage apparatus 146 and performs the data conversion process in a plurality of stages to generate shot data specific to the apparatus. To write a figure by the lithography apparatus 100, it is necessary to divide each figure defined in the pattern writing data into sizes that can be irradiated by one beam shot. Thus, the shot data generation unit 112 generates shot figures by dividing each figure into sizes that can be irradiated in one beam shot to actually write a pattern. Then, shot data is generated for each shot figure. In the shot data, for example, figure data such as the figure type, figure size, and irradiation position is defined.

As the dose operation process (S132), the dose operation unit 113 operates a dose d for each mesh region in a predetermined size. The dose d can be operated as a value obtained by multiplying the base doses of the beam Dbase by a correction coefficient. As the correction coefficient, for example, a proximity effect-corrected irradiation coefficient Dp may suitably be used. A conventional method may be used to operate the proximity effect-corrected irradiation coefficient Dp.

As the correction process (S134), the correction unit 115 operates a corrected dose corrected for each shot figure by multiplying the corresponding dose d by the modulated dose rate indicated by the index number defined for the figure as a base of the shot figure.

As the pattern writing process (S136), the pattern writing controller 114 outputs a control signal to a control circuit 120 to perform a pattern writing process. After shot data and data of each corrected dose being input, the control circuit 120 controls the pattern generator 150 according to a control signal from the pattern writing controller 114 and the pattern generator 150 writes the figure pattern on the target object 101 by using the electron beam 200. A more specific operation is as described below.

The electron beam 200 emitted from the electron gun assembly 201 (emission unit) illuminates the whole first aperture plate 203 having a rectangular hole through the illumination lens 202. Here, the electron beam 200 is first shaped into a rectangular shape. Then, the electron beam 200 of a first aperture image having passed through the first aperture plate 203 is projected on the second aperture plate 206 by the projection lens 204. The first aperture image on the second aperture plate 206 is controlled to deflect by the deflector 205 so that the beam shape and dimensions can be changed (variably shaped). Then, the electron beam 200 of a second aperture image having passed through the second aperture plate 206 is focused by the objective lens 207 and deflected by the main deflector 208 and the sub-deflector 209 before being shone on a desired position of the target object 101 arranged on the XY stage 105 moving continuously. In FIG. 1, a case in which a multi-stage deflector of the 2-stage main/sub-deflectors is used for position deflection is shown. In such a case, the electron beam 200 of the shot may be deflected by the main deflector 208 to the reference position of a sub-field (SF) obtained by further dividing a stripe region virtually while following the stage movement to deflect a beam of the shot to each irradiation position in the SF by the sub-deflector 209.

Figure 7:
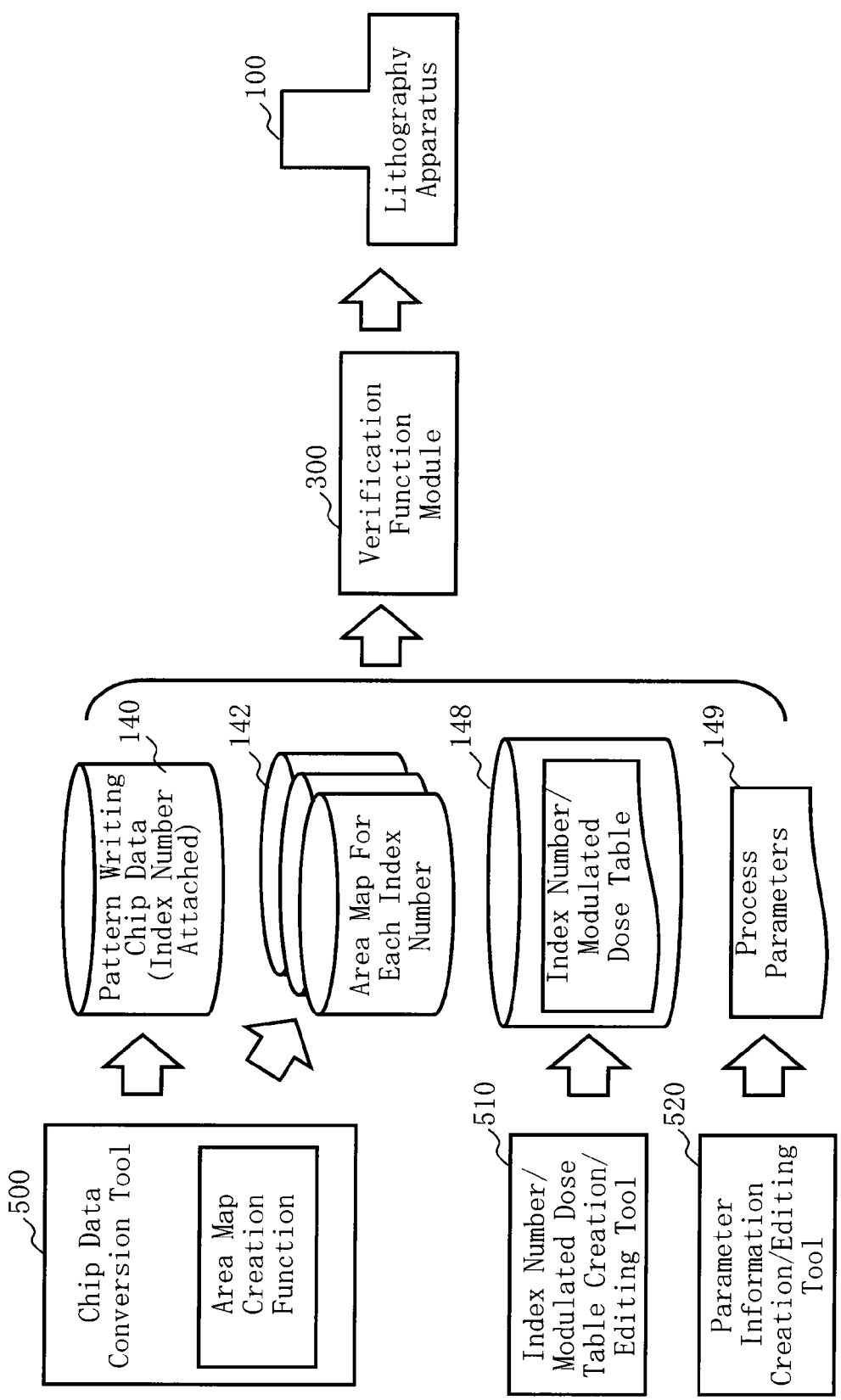

FIG. 7 is a conceptual diagram showing the configuration of a pattern writing system when the inspection method of pattern writing data in Embodiment 1 is focused on. As shown in FIG. 7, the pattern writing data conversion apparatus 500 converts layout data into pattern writing data and creates an area map. Then, the pattern writing data is stored in the storage apparatus 146 and the area map is stored in the storage apparatus 142. A modulated dose table creation tool 510 creates a modulated dose table and stores the table in the storage apparatus 148. A parameter information creation tool 520 creates parameter information containing process parameters and stores the information in the storage apparatus 149. The inspection apparatus 300 arranged off-line of the lithography apparatus 100 uses the above information to inspect pattern writing data for abnormalities. Then, the lithography apparatus 100 performs the pattern writing process by using the pattern writing data without abnormalities.

Figure 8:
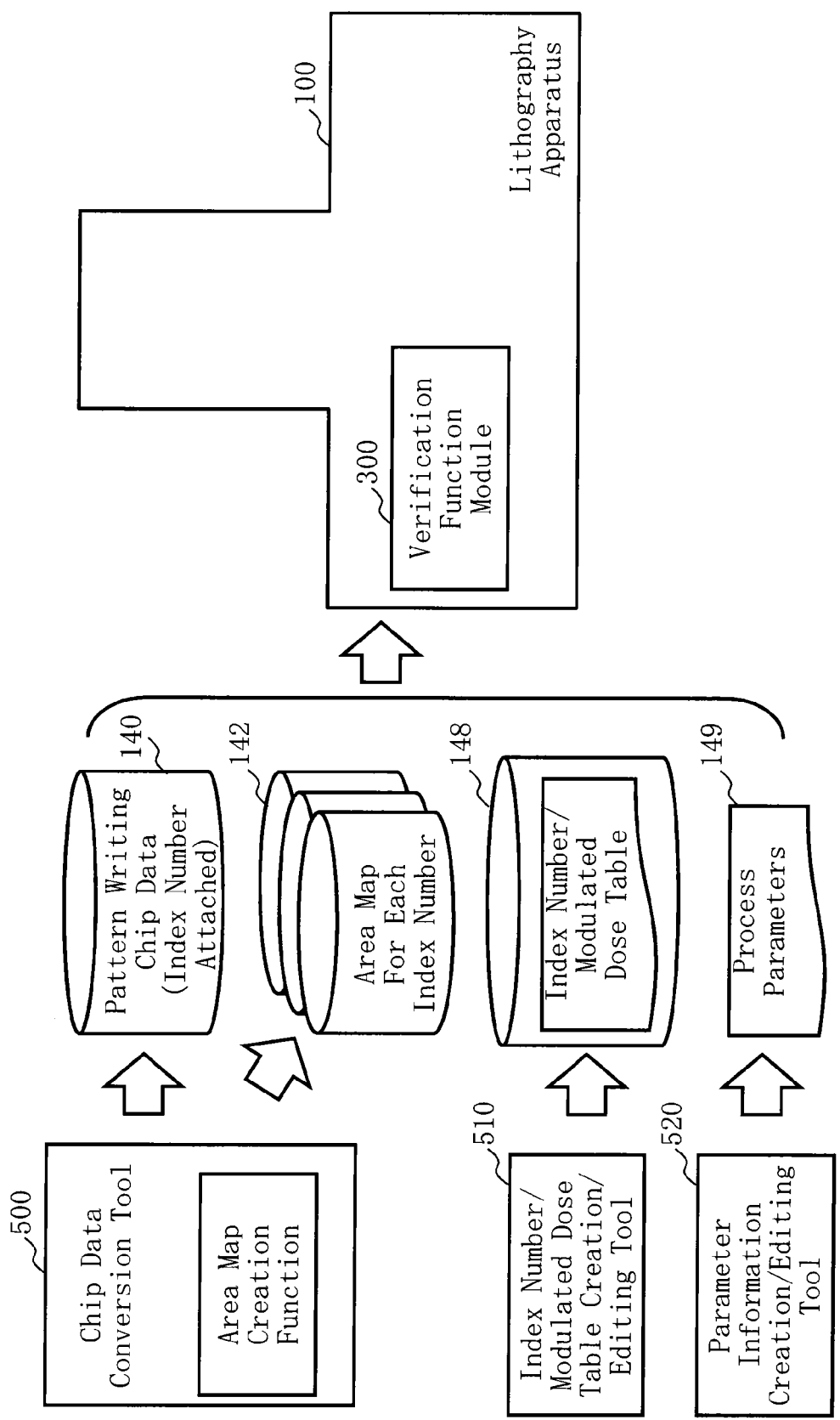

FIG. 8 is a conceptual diagram showing another example of the configuration of the pattern writing system when the inspection method of pattern writing data in Embodiment 1 is focused on. In Embodiment 1, as described with reference to FIG. 7, a case in which the inspection apparatus 300 is arranged off-line of the lithography apparatus 100, but as shown in FIG. 8, the inspection apparatus 300 may suitably be arranged inside the lithography apparatus 100. For example, each function of the control computer 310 may be arranged inside the control computer 110. Alternatively, the lithography apparatus 100 may include a plurality of control computers 119, 310. By including the inspection function of the input pattern writing data in the lithography apparatus 100, the pattern writing data can be inspected (S110 to S124) in parallel with the shot data generation process (S130). Accordingly, the time of the inspection (S110 to S124) of pattern writing data can be overlaid on the shot data generation process (S130). Accordingly, the pattern writing time can further be reduced. The time of the inspection (S110 to S124) of pattern writing data ends, as described above, in a few minutes and thus, the inspection ends in an early stage of the data conversion process in the shot data generation process (S130). Therefore, even if an abnormality of pattern writing data should be detected, wasted time can be limited to the shot data generation time of a few minutes.

According to Embodiment 1, as described above, beam irradiation of an abnormal dose due to pattern writing data input into a lithography apparatus can be avoided. As a result, abnormal pattern dimensions CD, resist evaporation, and lithography apparatus contamination (or a lithography apparatus failure) caused by beam irradiation of an abnormal dose can be avoided.

Embodiment 2

In Embodiment 2, a technique capable of further improving calculation accuracy of the amount of electric charge Q will be described.

Figure 9:
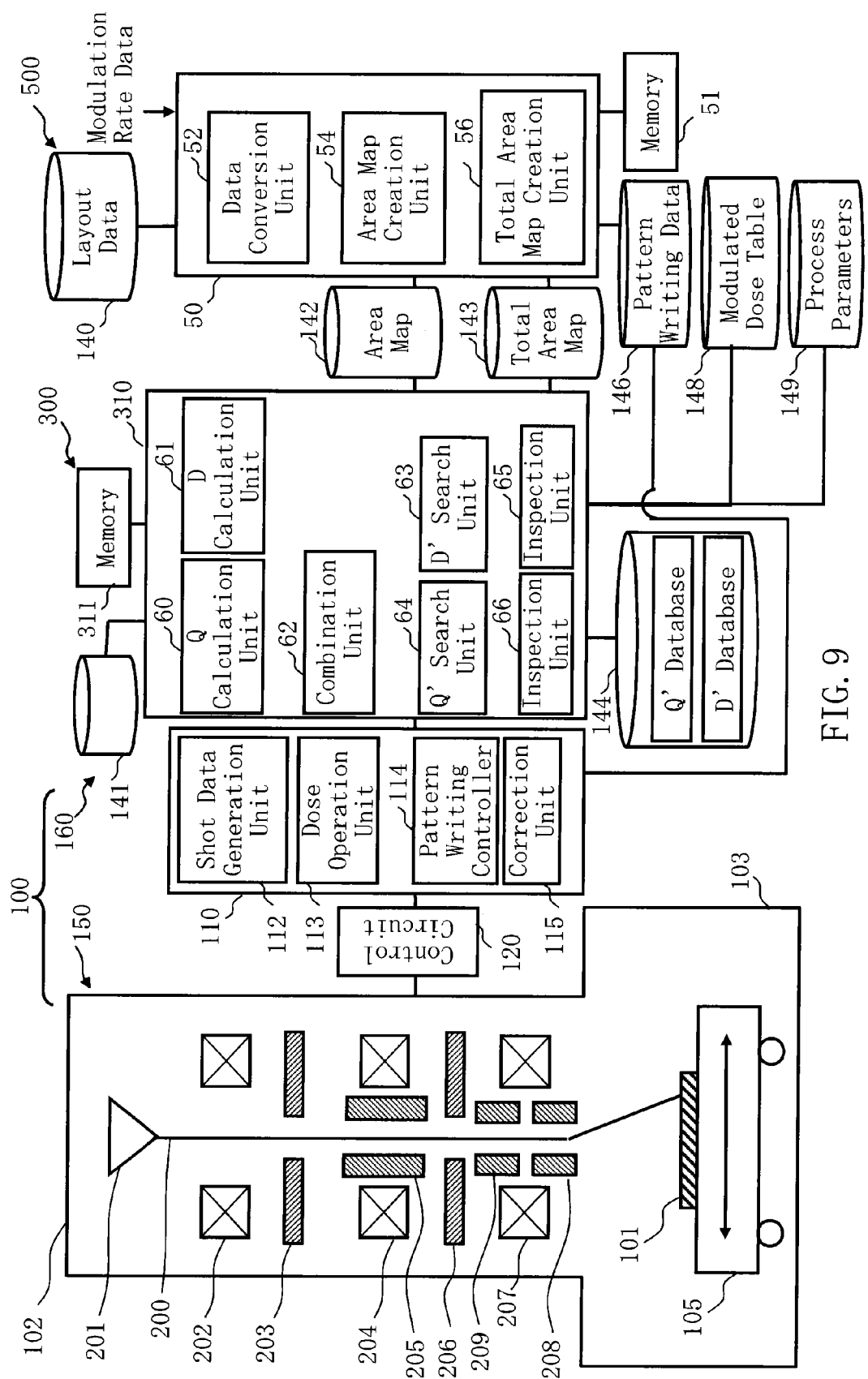
FIG. 9 is a conceptual diagram showing the configuration of the pattern writing system according to Embodiment 2.

FIG. 9 is a conceptual diagram showing the configuration of the pattern writing system according to Embodiment 2. FIG. 9 is the same as FIG. 1 except that a total area map creation unit 56 is added to the control computer 50 and a storage apparatus 143 is added.

Figure 10:
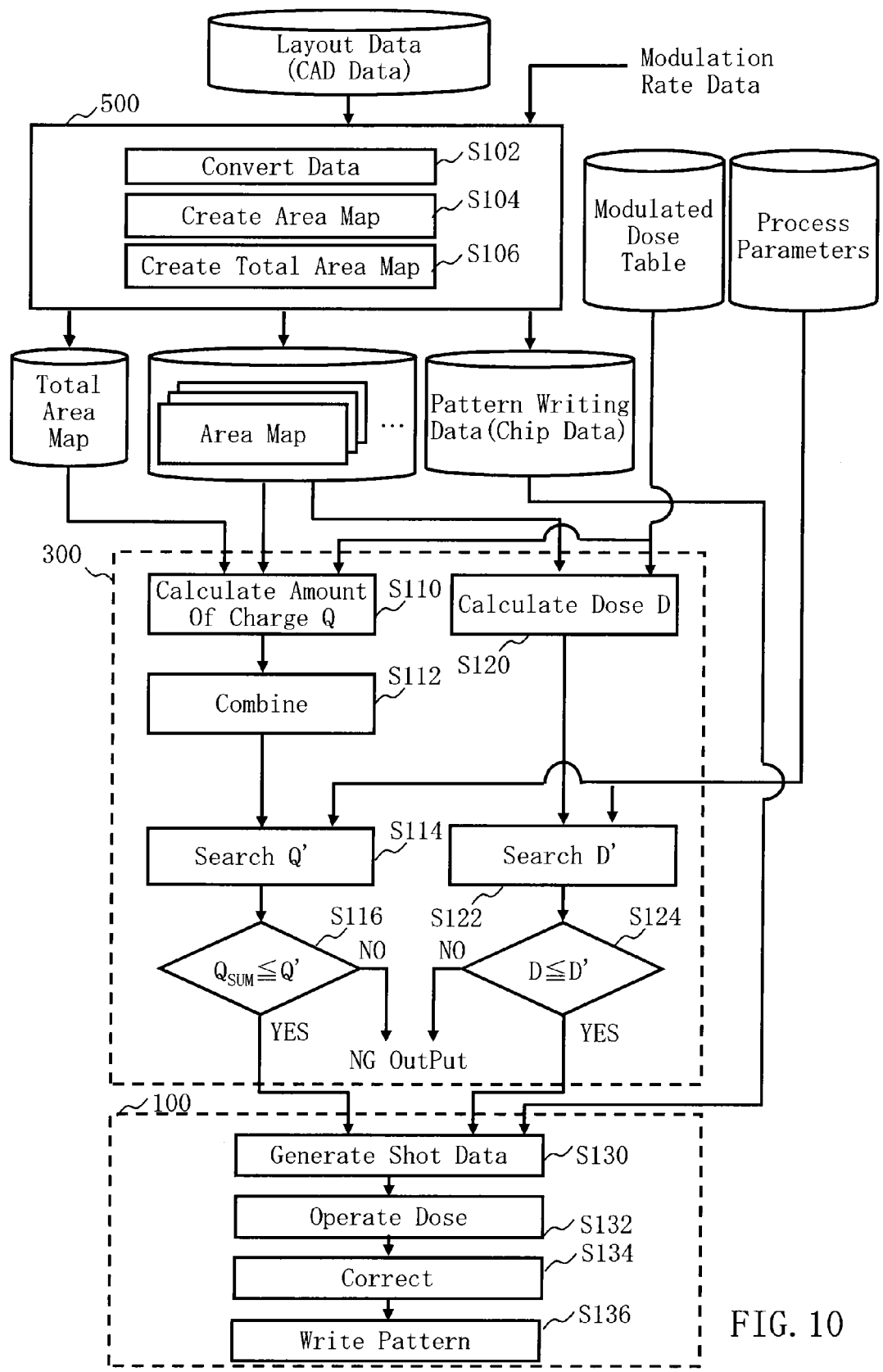
FIG. 10 is a flow chart showing principal processes from the data conversion of pattern writing data to the pattern writing process in Embodiment 2.

FIG. 10 is a flow chart showing principal processes from the data conversion of pattern writing data to the pattern writing process in Embodiment 2. FIG. 10 is the same as FIG. 5 except that a total area map creation process (S106) performed by the pattern writing data conversion apparatus 500 is added. The contents not specifically described below are the same as those in Embodiment 1.

As the total area map creation process (S106), the total area map creation unit 56 creates a total area map of figures written on the target object by using layout data while mixed regardless of the modulation rate to modulate the dose.

The total area map creation process (S106) is suitably performed in parallel with the data conversion process (S102). The total area map creation process (S106) may also be performed in parallel with the area map creation process (S104) or in series. In any case, the total area map creation time can be overlaid on the data conversion time by the total area map creation process (S106) being performed in parallel with the data conversion process (S102).

Figure 11:
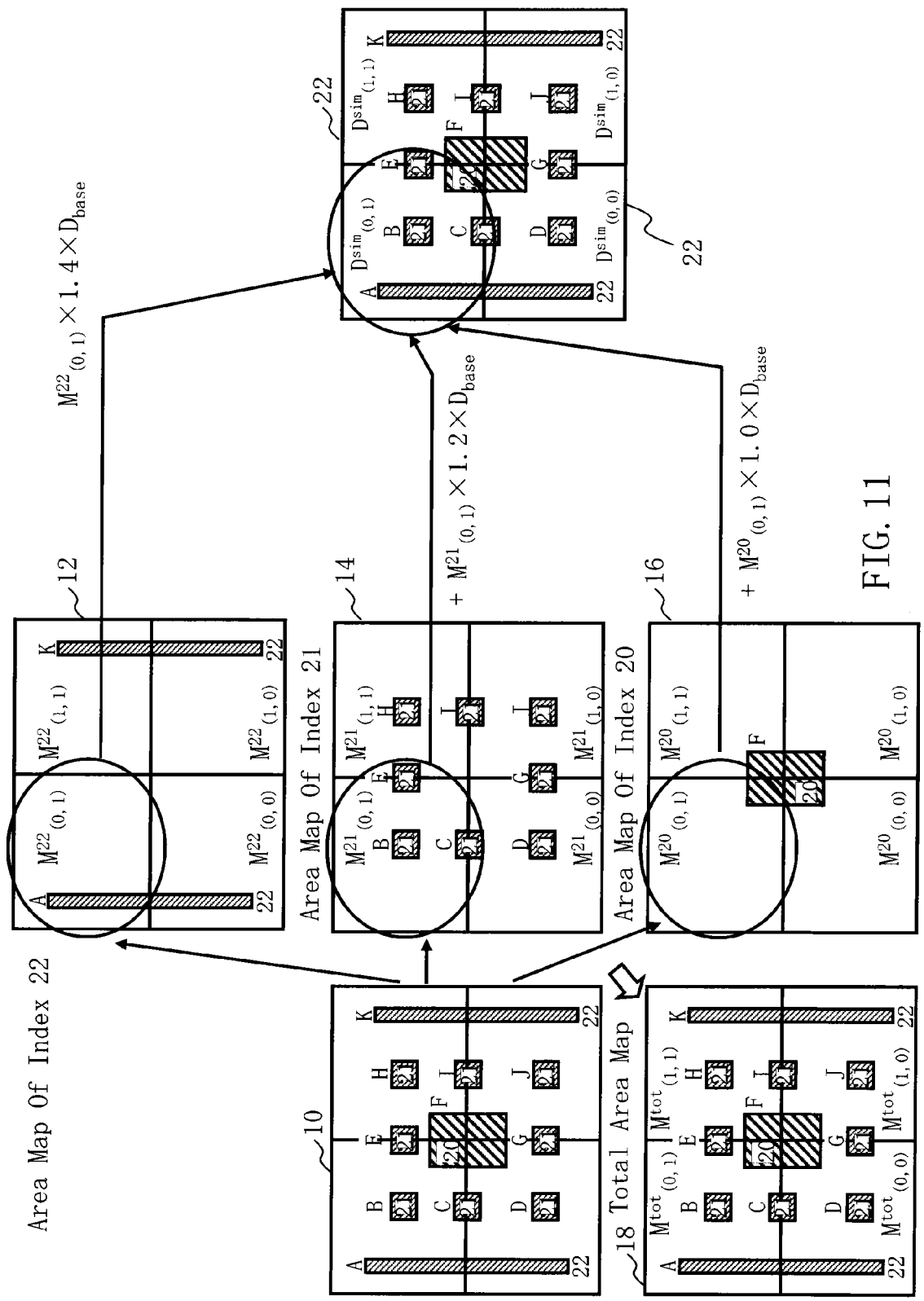
FIG. 11 is a conceptual diagram showing the flow of calculating the amount of electric charge in Embodiment 2.

FIG. 11 is a conceptual diagram showing the flow of calculating the amount of electric charge in Embodiment 2. In FIG. 11, in addition to the area maps 12, 14, 16 for each index number, an area map in a state in which figures of each index number are mixed regardless of the index number divided into mesh regions of the same size is created as a total area map 18. The created total area map 18 is stored in the storage apparatus 143.

As the charge amount Q calculation process (S110), the charge amount Q calculation unit 60 reads each area map from the storage apparatus 142, reads the total area map from the storage apparatus 143, and reads the modulated dose table from the storage apparatus 148 to calculate the amount of electric charge Q for each mesh region of each area map. In Embodiment 2, instead of using the base doses of the beam Dbase unchanged, a dose $D_{0(i,j)}$ obtained by correcting the base doses of the beam Dbase by using a total area $M_{tot(i,j)}$ in the mesh region and the proximity effect correction coeffi cients 11 is used for each mesh region of coordinates (i, j). The dose $D_{0(i,j)}$ is defined by Formula (2) below:

$$D_{0(i,j)} = Dbase \cdot (0.5+\eta)/(0.5+M_{tot(i,j)} \cdot \eta) \quad (2)$$

Then, the amount of electric charge $Q_{(i,j)}$ for each mesh region of the index number N is defined by Formula (3) below by using the area $M_{N(i,j)}$ in the mesh region, the modulated dose rate $R_N$ indicated by the index number N, and the dose $D_{0(i,j)}$.

$$Q_{(i,j)} = M_{N(i,j)} \cdot RN \cdot D_{0(i,j)} \quad (3)$$

Each calculated amount of electric charge $Q_{(i,j)}$ is stored in the storage apparatus 141. The base doses of the beam Dbase may be preset.

As the combination process (S112), the combination unit 62 combines the same mesh regions of the area maps 12, 14, 16 to create a combined map 22. The combination unit 62 adds up the amounts of electric charge $Q_{(i,j)}$ of the same mesh regions to calculate the total amount of electric charge $Qsum_{(i,j)}$. Accordingly, the amount of electric charge Qsum stored due to the electron beam 200 with which each mesh region is irradiated can be determined. As each mesh value of the combined map 22, each corresponding amount of electric charge $Qsum_{(i,j)}$ is defined. Hereinafter, Embodiment 2 is the same as Embodiment 1.

In Embodiment 2, the accuracy of the amount of electric charge $Q_{(i,j)}$ can be improved by using the dose $D_{0(i,j)}$ obtained by correcting the base doses of the beam Dbase by using the total area $M_{tot(i,j)}$ in the mesh region and the proximity effect correction coefficients η to calculate the amount of electric charge $Q_{(i,j)}$.

Embodiment 3

In Embodiment 3, a technique capable of further improving calculation accuracy of the amount of electric charge Q will be described.

Figure 12:
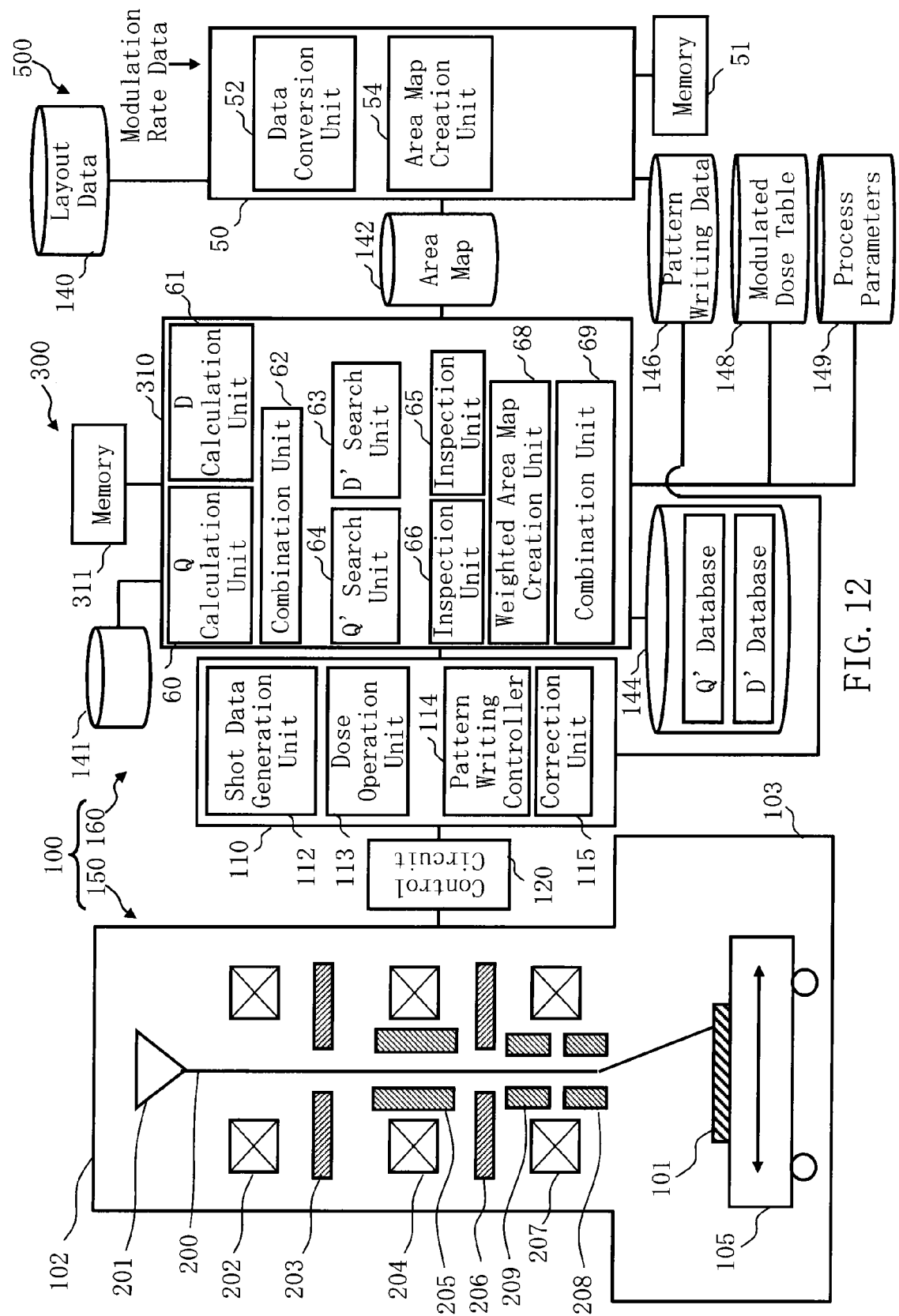
FIG. 12 is a conceptual diagram showing the configuration of the pattern writing system according to Embodiment 3.

FIG. 12 is a conceptual diagram showing the configuration of the pattern writing system according to Embodiment 3. FIG. 12 is the same as FIG. 1 except that a weighted area map creation unit 68 and a combination unit 69 are added to the control computer 310.

Figure 13:
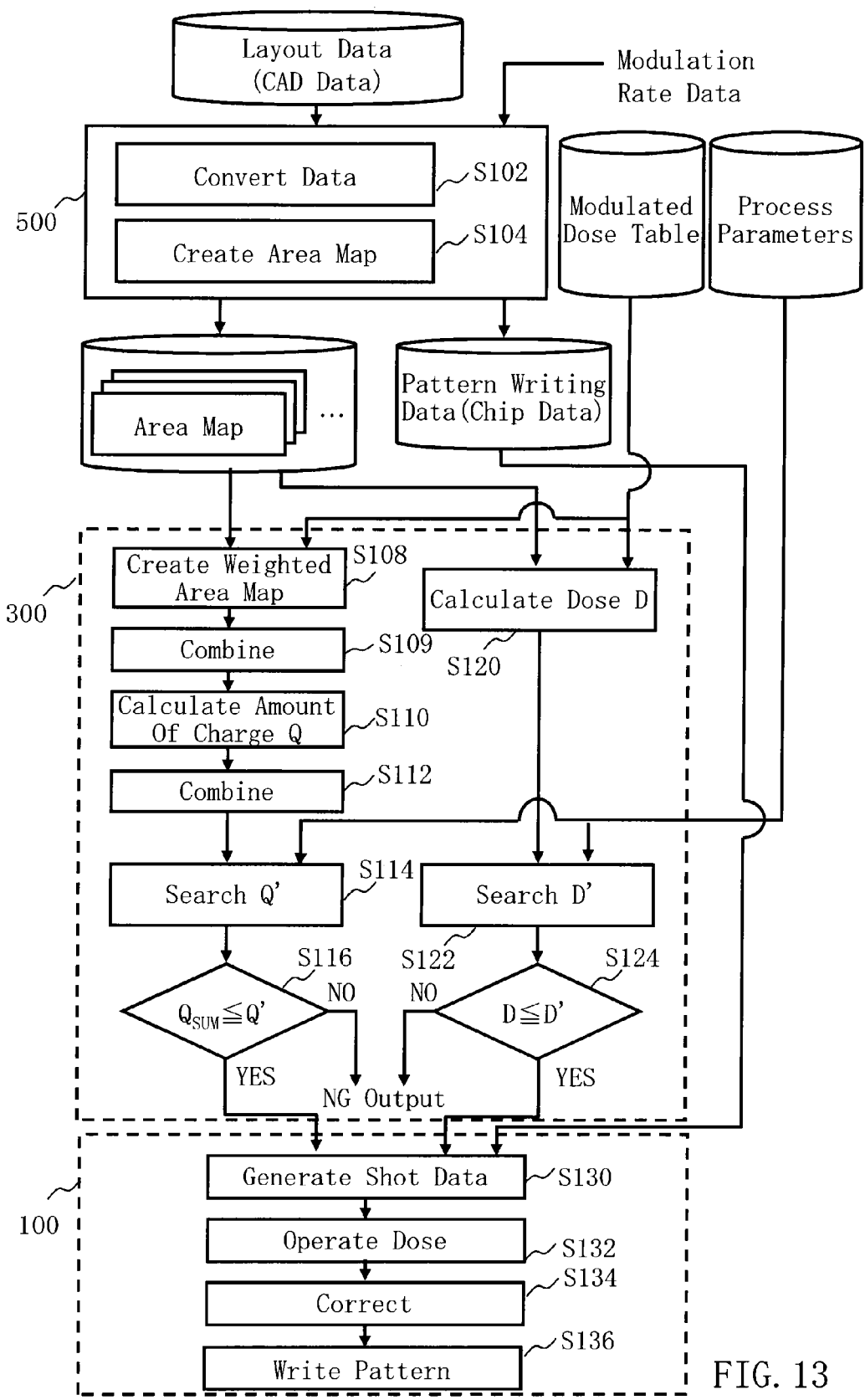
FIG. 13 is a flow chart showing principal processes from the data conversion of pattern writing data to the pattern writing process in Embodiment 3.

FIG. 13 is a flow chart showing principal processes from the data conversion of pattern writing data to the pattern writing process in Embodiment 3. FIG. 13 is the same as FIG. 5 except that a weighted area map creation process (S108) and a combination process (S109) are added before the charge amount Q calculation process (S110). The contents not specifically described below are the same as those in Embodiment 1.

Figure 14:
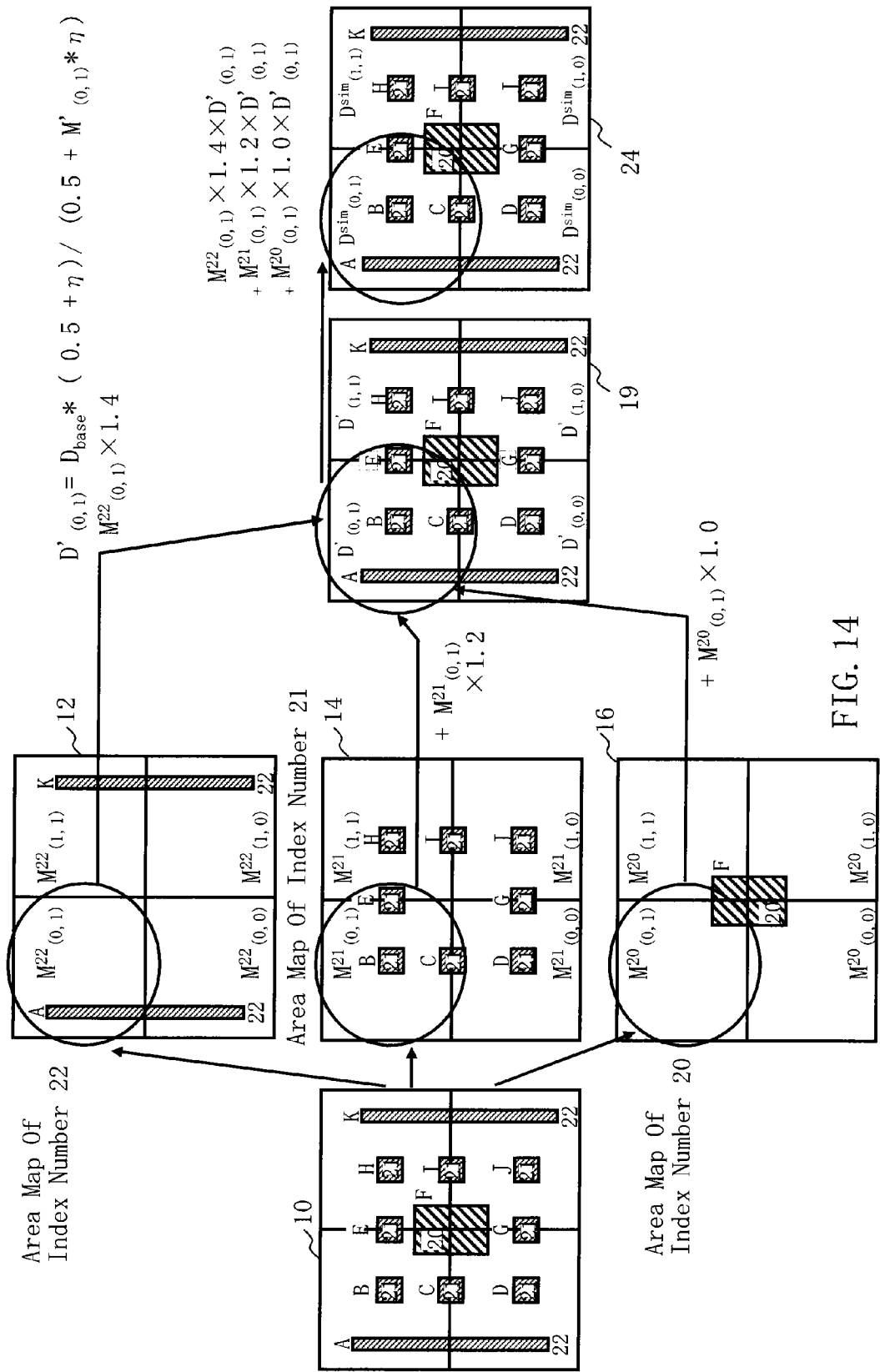
FIG. 14 is a conceptual diagram showing the flow of calculating the amount of electric charge in Embodiment 3.

FIG. 14 is a conceptual diagram showing the flow of calculating the amount of electric charge in Embodiment 3. In FIG. 14, a combined map 19 is created by assigning weights to area values by using the area maps 12, 14, 16 for each index number and combining the area maps 12, 14, 16.

As the weighted area map creation process (S108), a weighted area map creation unit 68 creates a weighted area map in which each area value is weighted by multiplying the area value $M_{N(i,j)}$ for each mesh region of the area maps 12, 14, 16 by the respective corresponding modulated dose rate $R_N$.

As the combination process (S109), the combination unit 69 combines the same mesh region of each weighted area map to create the combined map 19. The combination unit 69 adds up the weighted area values of the same mesh regions to calculate a total area value $M'_{(i,j)}$. In Embodiment 3, instead of the total area $M_{tot(i,j)}$ in Embodiment 2, the weighted total area value $M'_{(i,j)}$ is used.

As the electric charge amount Q calculation process (S110), the charge amount Q calculation unit 60 reads each area map from the storage apparatus 142, reads the total area map from the storage apparatus 143, and reads the modulated dose table from the storage apparatus 148 to calculate the amount of electric charge Q for each mesh region of each area map. In Embodiment 3, instead of using the base doses of the beam Dbase unchanged, a dose $D'_{0(i,j)}$ obtained by correcting the base doses of the beam Dbase by using a weighted total area value $M'_{(i,j)}$ in the mesh region and the proximity effect correction coefficients η for each mesh region of coordinates (i, j). The dose $D'_{0(i,j)}$ is defined by Formula (4) below:

$$D'_{0(i,j)} = Dbase \cdot (0.5+\eta)/(0.5+M'_{(i,j)} \cdot \eta) \quad (4)$$

Then, the amount of electric charge $Q_{(i,j)}$ for each mesh region of the index number N is defined by Formula (5) below by using the area $M_{N(i,j)}$ in the mesh region, the modulated dose rate $R_N$ indicated by the index number N, and the dose $D'_{0(i,j)}$.

$$Q_{(i,j)} = MN_{(i,j)} \cdot Rk \cdot D'_{0(i,j)} \quad (5)$$

Each calculated amount of electric charge $Q_{(i,j)}$ is stored in the storage apparatus 141. The base doses of the beam Dbase may be preset.

As the combination process (S112), the combination unit 62 combines the same mesh regions of the area maps 12, 14, 16 to create a combined map 24. The combination unit 62 adds up the amounts of electric charge $Q_{(i,j)}$ of the same mesh regions to calculate the total amount of electric charge $Qsum_{(i,j)}$. Accordingly, the amount of electric charge Qsum stored due to the electron beam 200 with which each mesh region is irradiated can be determined. As each mesh value of the combined map 24, each corresponding amount of electric charge $Qsum_{(i,j)}$ is defined. Hereinafter, Embodiment 3 is the same as Embodiment 1.

In Embodiment 3, the accuracy of the amount of electric charge $Q_{(i,j)}$ can be improved more than Embodiment 2 by using the dose $D'_{0(i,j)}$ obtained by correcting the base doses of the beam Dbase by using the weighted total area value $M'_{(i,j)}$ in the mesh region and the proximity effect correction coefficients η to calculate the amount of electric charge $Q_{(i,j)}$.

FIG. 15 is a diagram showing an example of the area map in each embodiment. For each mesh region (i, j) of the area map of the index number N, an area $M_{N(i,j)}$ of figures of the index number N is defined.

FIG. 16 is a diagram showing an example of a data structure of the area map in each embodiment. In the example of FIG. 16, each area $M_{N(i,j)}$ is defined for each ID of the mesh region in the order of index number. In the case of such a data structure, each of all mesh regions is inspected. However, there are some cases when no problem is expected even without inspecting all mesh regions, for example, without calculating the amount of electric charge Q, if the sum of areas for each index number is equal to or less than the threshold. Alternatively, the sum of areas for each index number may be sorted in descending order thereof to inspect only k largest areas. The inspection time can be shortened by omitting to read data from mesh regions that are not inspected. Thus, the data structure of an area map that can shorten the inspection time will be described below.

FIG. 17 is a diagram showing an example of the data structure of the area map in each embodiment. In FIG. 17, a skip flag field is added to the data structure in FIG. 16 to define each area $M_{N(i,j)}$ for each ID of the mesh region in the order of index number and further to define a flag indicating an inspection. For example, the value 0 defines that an inspection is carried out and the value 1 defines that an inspection is omitted. By adopting the above configuration, an inspection process of mesh regions for which the flag of value 1 is defined can be omitted.

FIG. 18 is a diagram showing another example of the data structure of the area map in each embodiment. In FIG. 18, a skip pointer field is added to the data structure in FIG. 16 to define a skip pointer for each ID of the mesh region after skipping. In the example of FIG. 18, a skip pointer P1 jumps to a skip pointer P2 of the mesh region of (0, 1). Thus, the inspection of mesh regions therebetween, (0, 0) to (2, 0), can be omitted.

Figure 19:
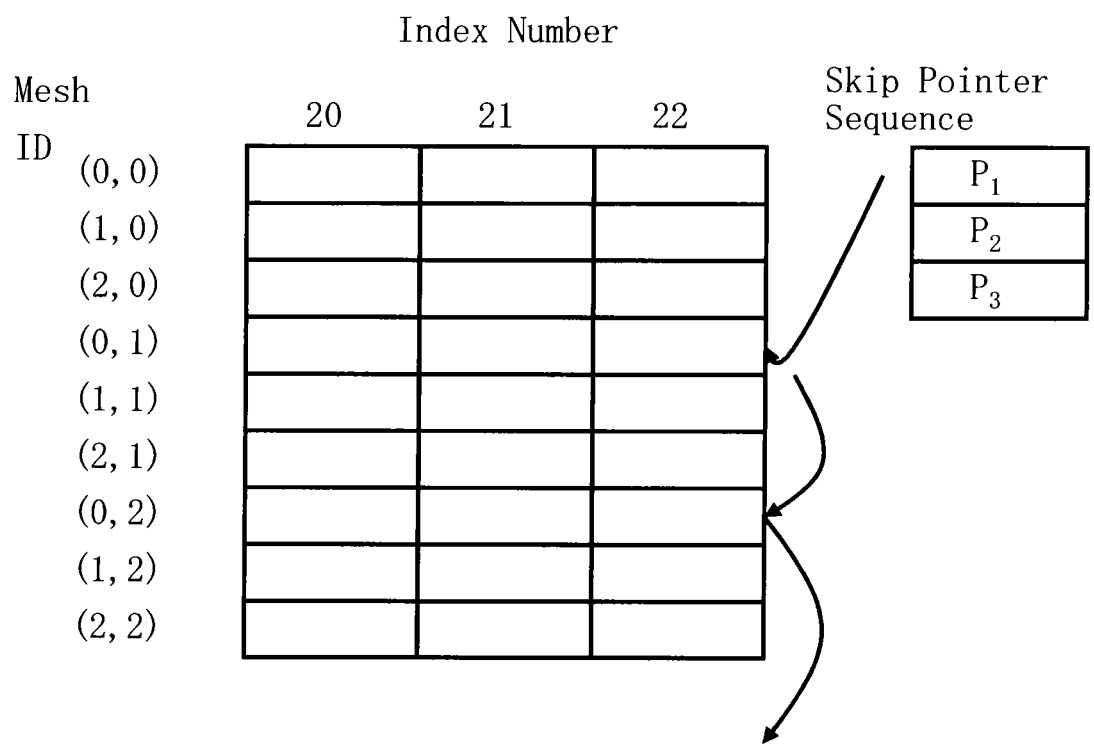
FIG. 19 is a diagram showing still another example of the data structure of the area map in Embodiments 1 to 3.

FIG. 19 is a diagram showing still another example of the data structure of the area map in each embodiment. While the skip pointer field is provided in FIG. 18, data of skip pointers is created as a separate file in FIG. 19. Then, data of IDs of mesh regions indicated by the data file of skip pointers may successively be read.

FIG. 20 is a diagram showing still another example of the data structure of the area map in each embodiment. FIG. 20 shows a data structure after data of skipped IDs of mesh regions being deleted from the data structure of area maps in FIG. 19. Accordingly, it is enough to inspect only defined data by using neither skip pointers nor flags.

FIG. 21 is a diagram showing still another example of the data structure of the area map in each embodiment. The ID of each mesh region is unknown in FIG. 20 and thus, it is difficult to identify the inspected mesh region. Thus, in FIG. 21, the data structure is created by retaining the ID of each mesh region. Accordingly, the mesh region where an abnormality is detected by an inspection can quickly be identified.

Embodiment 4

Figure 22:
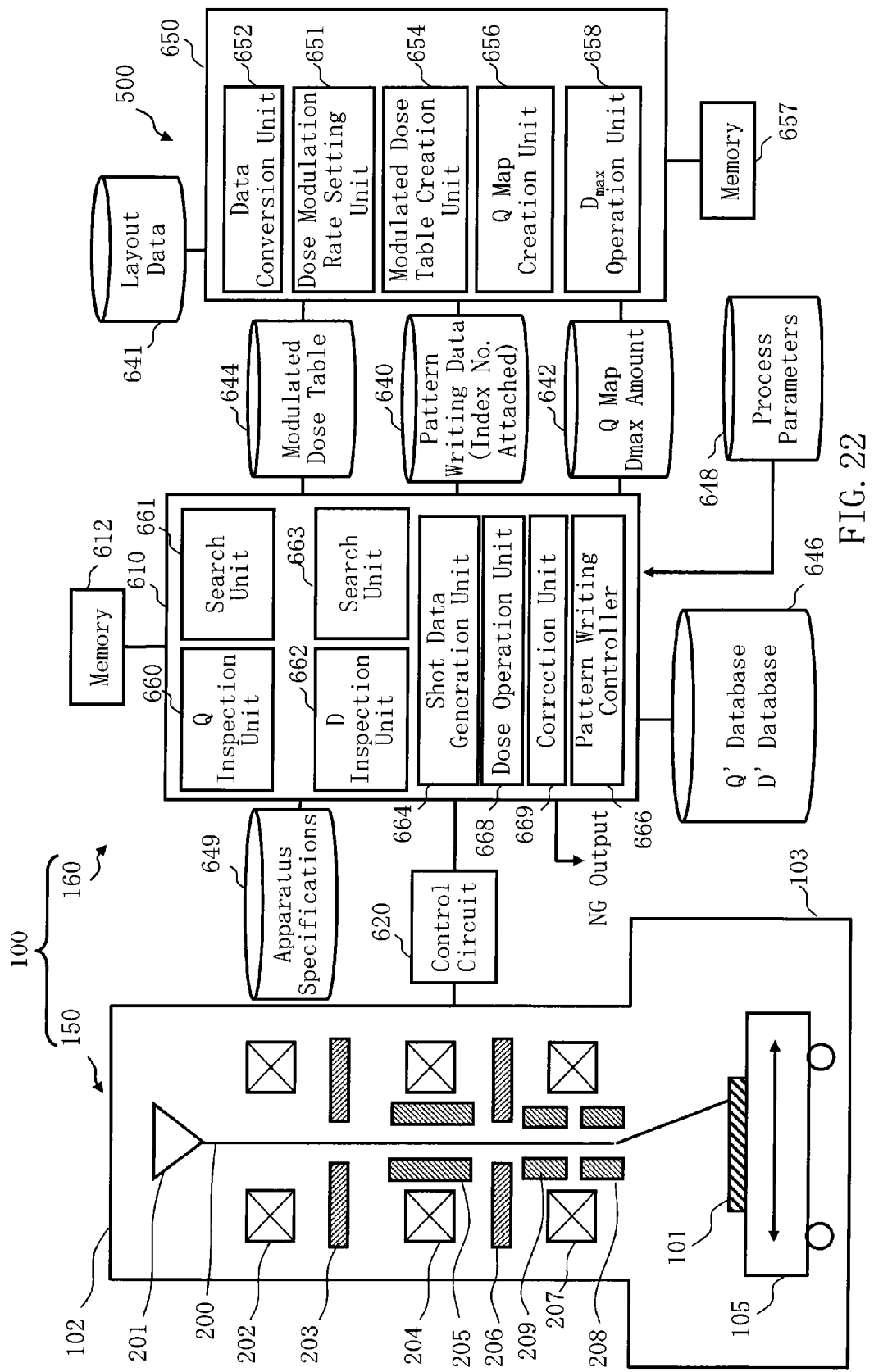
FIG. 22 is a conceptual diagram showing the configuration of the pattern writing system according to Embodiment 4.

FIG. 22 is a conceptual diagram showing the configuration of the pattern writing system according to Embodiment 4. In FIG. 22, the pattern writing system includes the lithography apparatus 100 and the pattern writing data conversion apparatus 500. In addition, a parameter information creation tool and the like (not shown) may also be included.

The lithography apparatus 100 includes the pattern generator 150 and the controller 160. The lithography apparatus 100 is an example of the charged particle beam lithography apparatus. Particularly, the lithography apparatus 100 is an example of the variable-shaped lithography apparatus. The pattern generator 150 includes the electron lens barrel 102 and the pattern writing chamber 103. In the electron lens barrel 102, the electron gun assembly 201, the illumination lens 202, the first aperture plate 203, the projection lens 204, the deflector 205, the second aperture plate 206, the objective lens 207, the main deflector 208, and the sub-deflector 209. The XY stage 105 is arranged inside the pattern writing chamber 103. The target object 101 such as a mask on which a pattern should be written is arranged on the XY stage 105 while a pattern is written. The target object 101 includes an exposure mask used for fabricating a semiconductor device. The target object 101 also includes mask blanks to which a resist is applied and on which no pattern is written.

The controller 160 includes a control computer 610, a memory 612, a control circuit 620, and storage apparatuses 640, 642, 644, 646 such as magnetic disk drives. The control computer 610, the memory 612, the control circuit 620, and the storage apparatuses 640, 642, 644, 646 are connected via a bus (not shown). A charge amount inspection unit 660, search units 661, 663, a dose inspection unit 662, a shot data generation unit 664, a pattern writing controller 666, a dose operation unit 668, and a correction unit 669 are arranged in the control computer 610. The function such as the charge amount inspection unit 660, the search units 661, 663, the dose inspection unit 662, the shot data generation unit 664, the pattern writing controller 666, the dose operation unit 668, and the correction unit 669 may be configured by hardware such as an electric circuit or by software such as a program executing these functions. Alternatively, the function may be configured by a combination of hardware and software. Information input into or output from the charge amount inspection unit 660, the search units 661, 663, the dose inspection unit 662, the shot data generation unit 664, the pattern writing controller 666, the dose operation unit 668, and the correction unit 669 and information during operation are stored in the memory 612 each time.

The pattern writing data conversion apparatus 500 includes a control computer 650, a memory 657, and a storage apparatus 641 such as a magnetic disk drive. The control computer 650, the memory 657, and the storage apparatus 641 are mutually connected via a bus (not shown). A data conversion unit 652, a dose modulation rate setting unit 651, a modulated dose table creation unit 654, a charge amount map creation unit 656, and a maximum dose operation unit 658 are arranged in the control computer 650. The function such as the data conversion unit 652, the dose modulation rate setting unit 651, the modulated dose table creation unit 654, the charge amount map creation unit 656, and the maximum dose operation unit 658 may be configured by hardware such as an electric circuit or by software such as a program executing these functions. Alternatively, the function may be configured by a combination of hardware and software. Information input into or output from the data conversion unit 652, the dose modulation rate setting unit 651, the modulated dose table creation unit 654, the charge amount map creation unit 656, and the maximum dose operation unit 658 and information during operation are stored in the memory 657 each time. In addition, layout data (for example, CAD data) as design data created by the user is stored in the storage apparatus 641.

The control computer 610 of the lithography apparatus 100 is connected to the pattern writing data conversion apparatus 500 and another storage apparatus 648 such as a magnetic disk drive via a network (not shown). Process parameters used when target layout data is written are stored in the storage apparatus 648. As process parameters, for example, the resist to be used or the like is defined.

Here, in FIG. 22, only the configuration needed to describe Embodiment 4 is shown. The lithography apparatus 100, the pattern writing data inspection apparatus 300, and the pattern writing data conversion apparatus 500 may normally include other necessary configurations. For example, a multi-stage deflector of the 2-stage main/sub-deflectors, the main deflector 208 and the sub-deflector 209, is used for position deflection, but a 1-stage deflector or a multi-stage deflector of three stages or more may be used for position deflection. In addition, an input apparatus such as a mouse or keyboard, a monitor apparatus, or an external interface circuit may be connected to the lithography apparatus 100 and the pattern writing data conversion apparatus 500.

It is necessary to convert layout data into pattern writing data that can be input into the lithography apparatus 100 to perform a pattern writing process in the lithography apparatus 100. Though not illustrated, the lithography apparatus 100 internally carries out a calculation of a dose correction such as a proximity effect correction, but a correction residual may still remain even if the dose calculated in the lithography apparatus is used. Thus, the user may particularly wish to additionally control the dose for a partial pattern or a local region, separately from other patterns or regions. In such a case, the modulated dose needs to be set by the user or correction tool or the like before data is input into the lithography apparatus.

Figure 23:
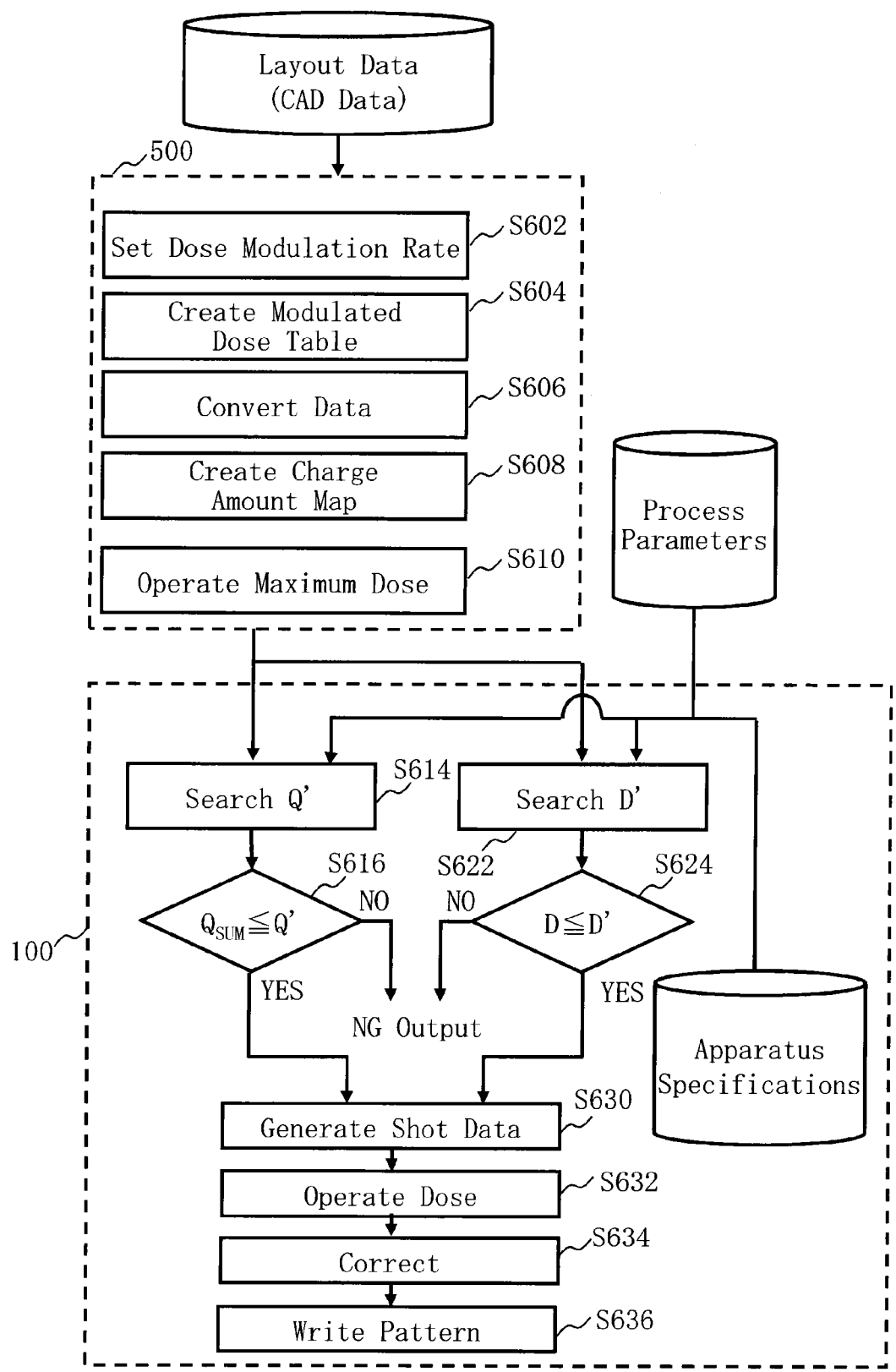
FIG. 23 is a flow chart showing principal processes of a method of writing a pattern according to Embodiment 4.

FIG. 23 is a flow chart showing principal processes of a method of writing a pattern according to Embodiment 4. As shown in FIG. 23, a dose modulation rate setting process (S602), a modulated dose table creation process (S604), a data conversion process (S606), a charge amount map creation process (S608), and a maximum dose operation process (S610) are performed by the pattern writing data conversion apparatus 500. Next, a threshold Q' search process (S614), an inspection process (S616), a threshold D' search process (S622), an inspection process (S624), a shot data generation process (S630), a dose operation process (S632), a correction process (S634), and a pattern writing process (S636) are performed by the lithography apparatus 100.

As shown in FIG. 2, for example, a plurality of figures A to K is arranged in layout data. Then, there may be a case when the figures A, K, the figures B to E, G to J, and the figure F should be written by using different doses. Thus, the modulated dose rate for the figures A, K, the modulated dose rate for the figures B to E, G to J, and the modulated dose rate for the figure F are preset. The dose after the modulation is calculated, for example, as a value obtained by multiplying the dose d after proximity effect corrections and the like being calculated inside the lithography apparatus 100 by the modulated dose rate. Therefore, the modulated dose table shown in FIG. 3 is created.

As shown in FIG. 2, an index number (identifier) is attached to each of a plurality of figures in the layout data. Then, as shown in FIG. 3, the modulated dose table has the modulated dose rate defined as a dose modulated amount for each index number. In FIG. 3, the modulated dose rate for the figure of the index number 20 is defined as 100%. The modulated dose rate for the figure of the index number 21 is defined as 120%. The modulated dose rate for the figure of the index number 22 is defined as 140%.

However, if many modulated dose segments should be set, manual work by the user is limited. For example, the dose modulation is performed by dividing figures into about 20 gradation segments. Thus, in Embodiment 4, the pattern writing data conversion apparatus 500 also sets the modulated dose rate.

Therefore, in the dose modulation rate setting process (S602), the dose modulation rate setting unit 651 sets the dose modulation rate to each of a plurality of figures defined for layout data. Settings of the dose modulation rate may be optimized based on past track record data or simulations.

Then, in the modulated dose table creation process (S604), the modulated dose table creation unit 654 creates an associated modulated dose table after modulation rate data of set modulated dose rates and the index numbers of corresponding figures being input. The modulated dose table is output and stored in the storage apparatus 644.

Then, in the data conversion process (S606), the data conversion unit 652 reads layout data (design data) in which a plurality of figures is defined from the storage apparatus 641 and converts the data into pattern writing data in a format that can be input into the lithography apparatus 100. The generated pattern writing data is output and stored in the storage apparatus 140.

In the generated pattern writing data, as shown in FIG. 2, the index number (identifier) to identify the modulated dose rate (modulation rate) is attached to each figure as additional data. Alternatively, figures for which the modulated dose rate is defined and figures for which no modulated dose rate is defined may be mixed. In the case in which both types of figures are mixed, a predetermined modulated dose rate is used for figures for which no modulated dose rate is defined. For example, the modulated dose rate of 100% may be used.

A plurality of chips may be arranged in the one target object 101. Thus, layout data contains a plurality of pieces of chip data. For this case, the modulated dose rate may suitably be set for each chip. In such a case, the index number (identifier) to identify the modulated dose rate (modulation rate) is attached to each chip as additional data in the generated pattern writing data. Also in such a case, chips for which the modulated dose rate is defined and chips for which no modulated dose rate is defined may be mixed. In the case in which both types of chips are mixed, a predetermined modulated dose rate is used for chips for which no modulated dose rate is defined. For example, the modulated dose rate of 100% may be used. Alternatively, the index number may naturally be defined for each figure constituting a chip as additional data.

In the charge amount map creation process (S608), the charge amount map creation unit 656 divides an arrangement region of the layout data 10 into mesh regions of a predetermined size. Then, the charge amount map creation unit 656 operates the amount of electric charge Q stored in the mesh region of coordinates (i, j) by irradiation of an electron beam for each mesh region. Then, the charge amount map creation unit 656 creates an electric charge amount map summarizing the amount of electric charge Q in each mesh region. The amount of electric charge Q in each mesh region may be calculated by operating a value obtained by multiplying the area $M_{(i,j)}$ of the figure, the modulated dose rate $R_N$ indicated by the index number N, and the base doses of the beam Dbase together for each figure in the mesh region and adding up an operation result of each figure in the mesh region. Instead of the base doses of the beam Dbase, the corrected dose $D_{O(i,j)}$ may be used. For example, the dose $D_{O(i,j)}$ obtained by correcting the base doses of the beam Dbase by using the total area $M_{tot(i,j)}$ in the mesh region and the proximity effect correction coefficients η may be used for each mesh region of coordinates (i, j). The dose $D_{O(i,j)}$ is defined by the above Formula (2).

Alternatively, the dose $D'_{O(i,j)}$ obtained by correcting the base doses of the beam Dbase by using the total area value $M'_{(i,j)}$ of area values weighted by multiplying the area of each figure in the mesh region by the corresponding modulated dose rate $R_N$ and the proximity effect correction coefficients η may be used for each mesh region of coordinates (i, j). The dose $D'_{O(i,j)}$ is defined by the above Formula (4).

Alternatively, the amount of electric charge Q of each mesh region may be determined by other calculation methods. The electric charge amount map is created as described above and stored in the storage apparatus 642.

The data conversion process and the charge amount map creation process are suitably performed in parallel. Generally, the conversion process from layout data into pattern writing data needs a few tens of hours. For example, about 20 hours are needed. Then, a few hours, for example, about five hours are needed for the electric charge amount map creation. Thus, by performing the data conversion process and the charge amount map creation process in parallel, the charge amount map creation time can be overlaid on the data conversion process time from layout data into pattern writing data. That is, the charge amount map creation time does not have to be added to the conventional pattern writing work time.

In the maximum dose operation process (S610), the maximum dose operation unit 658 operates the maximum dose Dmax when a pattern is written in the set dose modulation rate. For example, the value obtained by multiplying the maximum value of the modulated dose rate $R_N$ by the base doses of the beam Dbase is operated. Alternatively, the maximum dose Dmax may be determined by other calculation methods. The value of the maximum dose Dmax is stored in the storage apparatus 642.

If the modulated dose rate in an operation result of the dose modulation rate setting unit 651 is incorrect, when such a value is input into the lithography apparatus and the value is used by the lithography apparatus unchanged, a beam of an abnormal dose will be shone. Beam irradiation of such an abnormal dose causes storage of an abnormal amount of electric charge in the mesh regions. Accordingly, abnormalities of the pattern dimensions CD are caused. Further, if the dose is an extremely abnormal value, resist evaporation and by extension, lithography apparatus contamination (or a lithography apparatus failure) could be caused by such evaporation. Thus, in Embodiment 4, the amount of electric charge is inspected for abnormalities before the data conversion process is performed in the lithography apparatus 100 or before the data conversion process is completed. Similarly, whether the irradiated maximum dose itself is an abnormal value is inspected.

First, in the threshold Q' search process (S614), the search unit 661 reads process parameters from the storage apparatus 648 storing process parameters and reads apparatus specifications from the lithography apparatus 100 to search for the charge amount threshold Q' indicating the maximum amount of electric charge that can be used for such process parameters and apparatus specifications by referring to the charge amount threshold Q' database (correlated data) stored in the storage apparatus 646. The maximum amount of electric charge that can be used changes depending on apparatus specifications of the lithography apparatus 100. Apparatus specifications may be different depending on the lithography apparatus to be used. For example, apparatus specifications are different from model to model. Variations of the maximum amount of electric charge that can be used may be present even for the same model. Similarly, the maximum amount of electric charge that can be used is different depending on process parameters, for example, the resist type. Thus, the search unit 661 uses information (for example, search keywords) of these process parameters and apparatus specifications to search for the charge amount threshold Q' indicating the maximum amount of electric charge that can be used.

Then, in the inspection process (S616), the charge amount inspection unit 660 reads the electric charge amount map from the storage apparatus 642 to inspect (judge) whether the amount of electric charge Q is equal to or less than the charge amount threshold Q' for each mesh region. If, as a result of the inspection, the amount of electric charge Q is larger than the charge amount threshold Q' in one of the mesh regions, error information is output as rejected pattern writing. If the amount of electric charge Q is equal to or less than the charge amount threshold Q' in all mesh regions, the lithography apparatus 100 is assumed to be able to perform a pattern writing process and OK information may be output to the pattern writing controller 666. In this manner, the charge amount inspection unit 660 inspects the amount of electric charge of each mesh region (predetermined region) when a pattern is written on a target object by using a electric charge amount map.

Also, in the threshold D' search process (S622), the search unit 663 reads process parameters from the storage apparatus 648 storing process parameters and reads apparatus specifications from the lithography apparatus 100 to search for the maximum dose threshold D' indicating the maximum dose that can be used for such process parameters and apparatus specifications by referring to the maximum dose threshold D' database (correlated data) stored in the storage apparatus 646. The maximum dose that can be used changes depending on apparatus specifications of the lithography apparatus 100. Apparatus specifications may be different depending on the lithography apparatus to be used. For example, apparatus specifications are different from model to model. Variations of the maximum dose that can be used may be present even for the same model. Similarly, the maximum dose that can be used is different depending on process parameters, for example, the resist type. Thus, the search unit 663 uses information (for example, search keywords) of these process parameters and apparatus specifications to search for the maximum dose threshold D' indicating the maximum dose that can be used.

Then, in the inspection process (S624), the dose inspection unit 662 (maximum dose inspection unit) reads the maximum dose from the storage apparatus 642 to inspect (judge) whether the maximum dose Dmax is equal to or less than the maximum dose threshold D'. If, as a result of the inspection, the maximum dose is larger than the maximum dose threshold D', error information is output as rejected pattern writing. If the maximum dose is equal to or less than the maximum dose threshold D', the lithography apparatus 100 is assumed to be able to perform a pattern writing process and OK information may be output to the pattern writing controller 666. In this manner, the dose inspection unit 662 inspects the maximum dose for each mesh region (predetermined region) when a pattern is written on a target object by using maximum dose data input from outside. Pattern writing data can be inspected for abnormalities by the above inspection process before the data conversion process of the pattern writing data in the lithography apparatus 100. Accordingly, useless work time in the lithography apparatus 100 can subsequently be avoided. Such an inspection process can be completed in a few minutes. Therefore, pattern writing data can be inspected for abnormalities in an early stage. If an electric charge amount map is created by the lithography apparatus 100, the charge amount map creation time is further added and the inspection time increases for the added time. In Embodiment 4, by contrast, an electric charge amount map is created at the same time as the generation of pattern writing data by, instead of the lithography apparatus 100, the pattern writing data conversion apparatus 500 upstream thereof and thus, only a few minutes are needed for the inspection of pattern writing data needed for the inspection process. Then, when the pattern writing data is inspected with no abnormality found, the pattern writing process is performed by the lithography apparatus 100.

In the above example, the charge amount threshold Q' and the maximum dose threshold D' when both of process information and apparatus specification information match are used, but the present embodiment is not limited to such an example. The charge amount threshold Q' and the maximum dose threshold D' when at least one of process information and apparatus specification information matches may also be used.

As the shot data generation process (S630), the shot data generation unit 664 reads pattern writing data from the storage apparatus 640 and performs the data conversion process in a plurality of stages to generate shot data specific to the apparatus. To write a figure by the lithography apparatus 100, it is necessary to divide each figure defined in the pattern writing data into sizes that can be irradiated by one beam shot. Thus, the shot data generation unit 664 generates shot figures by dividing each figure into sizes that can be irradiated in one beam shot to actually write a pattern. Then, shot data is generated for each shot figure. In the shot data, for example, figure data such as the figure type, figure size, and irradiation position is defined.

As the dose operation process (S632), the dose operation unit 668 operates the dose d for each mesh region in a predetermined size. The dose d can be operated as a value obtained by multiplying, for example, the base doses of the beam Dbase by a correction coefficient. As the correction coefficient, for example, the proximity effect-corrected irradiation coefficient Dp may suitably be used. A conventional method may be used to operate the proximity effect-corrected irradiation coefficient Dp.

As the correction process (S634), the correction unit 669 operates a corrected dose corrected for each shot figure by multiplying the corresponding dose d by the modulated dose rate indicated by the index number defined for the figure as a base of the shot figure.

As the pattern writing process (S636), the pattern writing controller 666 outputs a control signal to a control circuit 620 to perform a pattern writing process. After shot data and data of each corrected dose being input, the control circuit 620 controls the pattern generator 150 according to a control signal from the pattern writing controller 666 and the pattern generator 150 writes the figure on the target object 101 by using the electron beam 200 based on pattern writing data paired with the electric charge amount map. A more specific operation is as described below.

The electron beam 200 emitted from the electron gun assembly 201 (emission unit) illuminates the whole first aperture plate 203 having a rectangular hole through the illumination lens 202. Here, the electron beam 200 is first shaped into a rectangular shape. Then, the electron beam 200 of a first aperture image having passed through the first aperture plate 203 is projected on the second aperture plate 206 by the projection lens 204. The first aperture image on the second aperture plate 206 is controlled to deflect by the deflector 205 so that the beam shape and dimensions can be changed (variably shaped). Then, the electron beam 200 of a second aperture image having passed through the second aperture plate 206 is focused by the objective lens 207 and deflected by the main deflector 208 and the sub-deflector 209 before being shone on a desired position of the target object 101 arranged on the XY stage 105 moving continuously. In FIG. 22, a case in which a multi-stage deflector of the 2-stage main/sub-deflectors is used for position deflection is shown. In such a case, the electron beam 200 of the shot may be deflected by the main deflector 208 to the reference position of a sub-field (SF) obtained by further dividing a stripe region virtually while following the stage movement to deflect a beam of the shot to each irradiation position in the SF by the sub-deflector 209.

According to Embodiment 4, as described above, beam irradiation of an abnormal dose due to pattern writing data input into a lithography apparatus can be avoided. As a result, abnormal pattern dimensions CD, resist evaporation, and lithography apparatus contamination (or a lithography apparatus failure) caused by beam irradiation of an abnormal dose can be avoided.

Embodiment 5

In Embodiment 4, the amount of electric charge and the maximum does are inspected in the lithography apparatus 100, but the inspection is not limited to the lithography apparatus 100. In Embodiment 5, a case in which a function unit that performs an inspection process is arranged off-line and configured as an inspection apparatus separately from the lithography apparatus 100 will be described.

Figure 24:
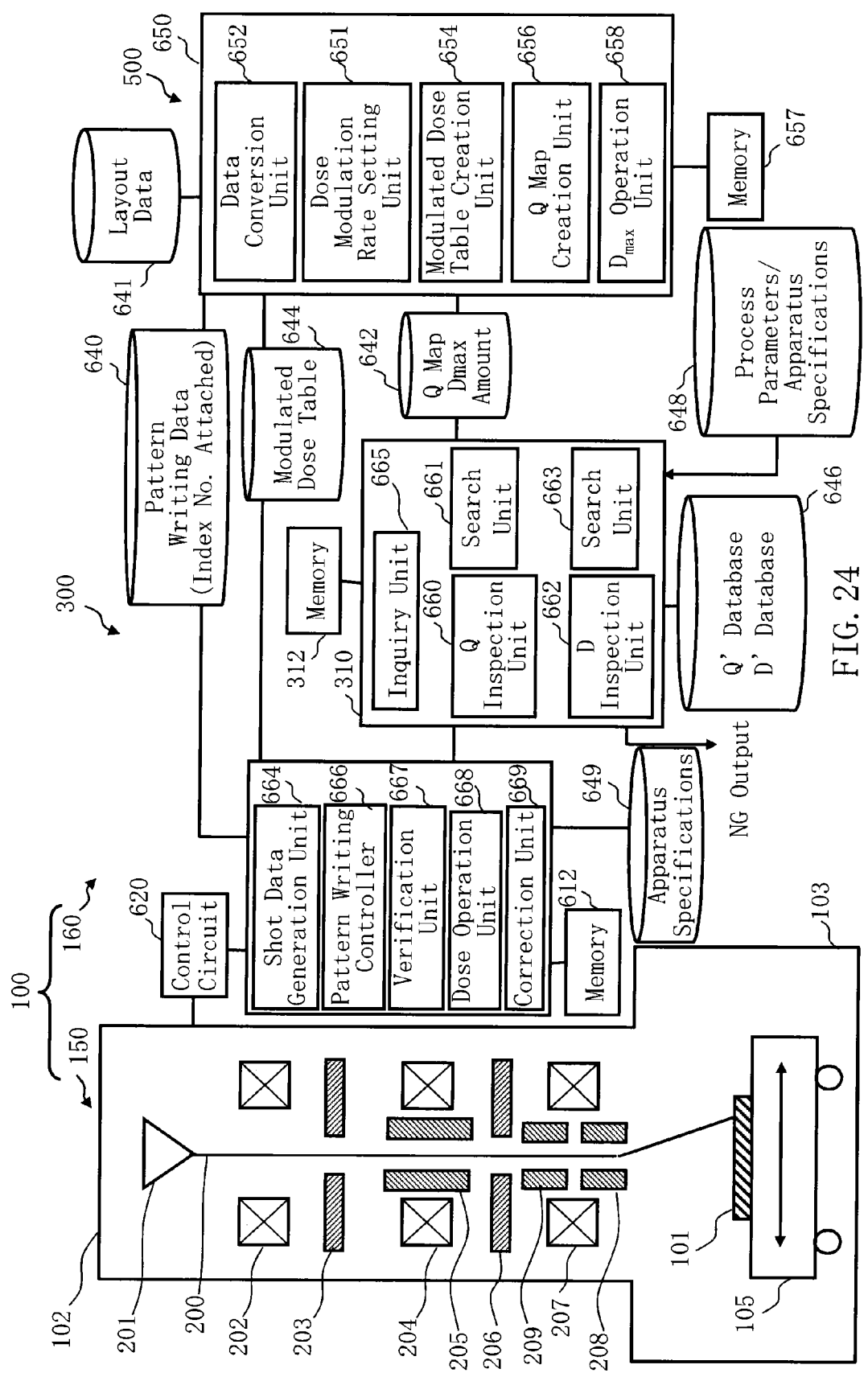
FIG. 24 is a conceptual diagram showing the configuration of the pattern writing system according to Embodiment 5.

FIG. 24 is a conceptual diagram showing the configuration of the pattern writing system according to Embodiment 5. In FIG. 24, the pattern writing system includes the lithography apparatus 100, the inspection apparatus 300, and the pattern writing data conversion apparatus 500. In addition, a parameter information creation tool and the like (not shown) may also be included. In FIG. 24, the inspection apparatus 300 includes the control computer 310 and a memory 312. Also, the storage apparatuses 642, 646 are changed from the configuration of the lithography apparatus 100 to the configuration of the inspection apparatus 300. In addition, the charge amount inspection unit 660, the search units 661, 663, and the dose inspection unit 662 are changed from the configuration of the lithography apparatus 100 to the configuration of the inspection apparatus 300. Thus, the charge amount inspection unit 660, the search units 661, 663, and the dose inspection unit 662 are arranged in the control computer 310. Further, an inquiry unit 665 is arranged in the control computer 310. The function such as the charge amount inspection unit 660, the search units 661, 663, the dose inspection unit 662, and the inquiry unit 665 may be configured by hardware such as an electric circuit or by software such as a program executing these functions. Alternatively, the function may be configured by a combination of hardware and software. Information input into or output from the charge amount inspection unit 660, the search units 661, 663, the dose inspection unit 662, and the inquiry unit 665 and information during operation are stored in the memory 312 each time.

Further, a verification unit 667 is arranged in the control computer 610. The function such as the shot data generation unit 664, the pattern writing controller 666, the verification unit 667, the dose operation unit 668, and the correction unit 669 may be configured by hardware such as an electric circuit or by software such as a program executing these functions. Alternatively, the function may be configured by a combination of hardware and software. Information input into or output from the shot data generation unit 664, the pattern writing controller 666, the verification unit 667, the dose operation unit 668, and the correction unit 669 and information during operation are stored in the memory 612 each time.

In FIG. 24, the other configuration is the same as in FIG. 22. The contents not specifically described below are the same as those in Embodiment 4.

Figure 25:
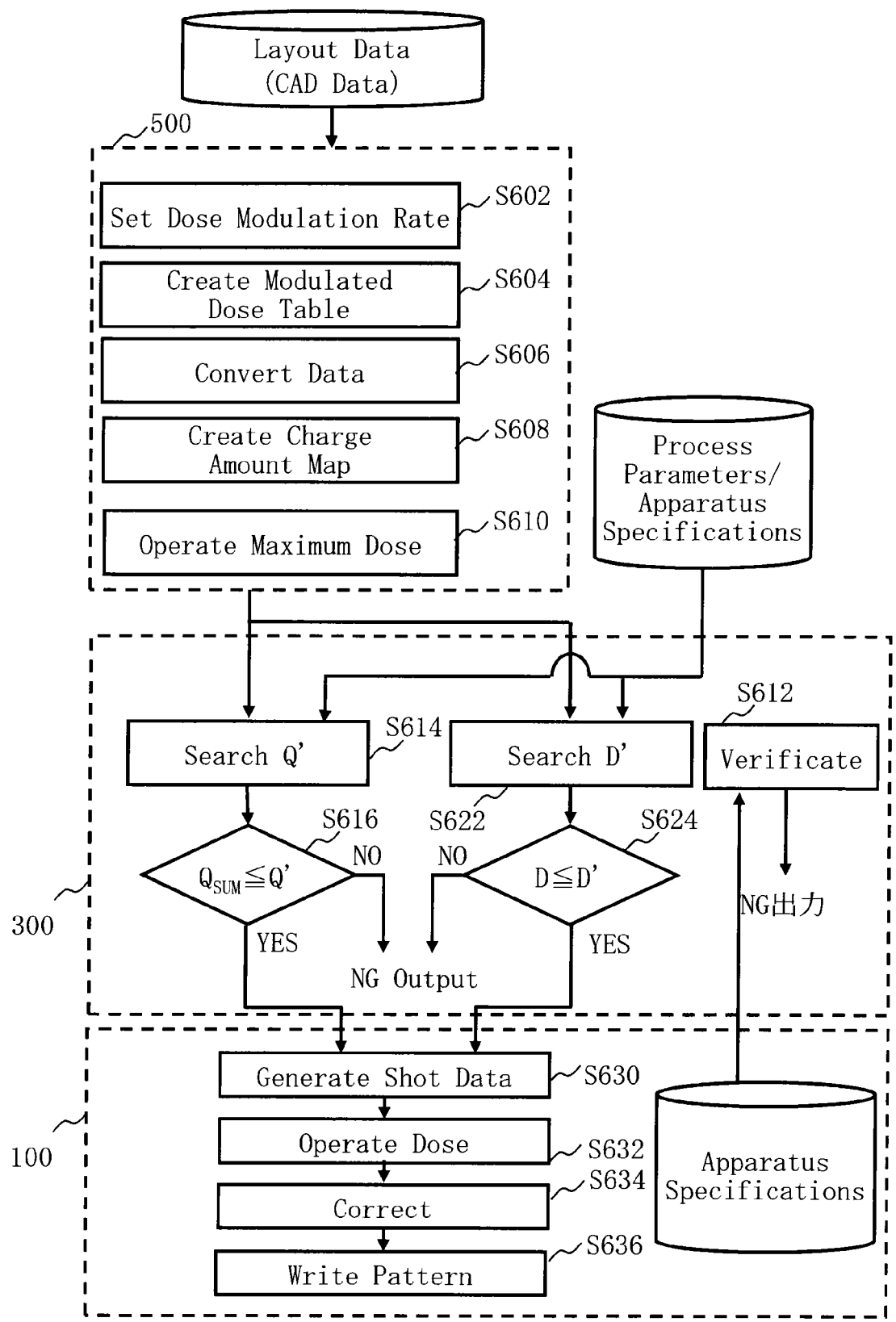
FIG. 25 is a flow chart showing principal processes of the method of writing a pattern according to Embodiment 5.

FIG. 25 is a flow chart showing principal processes of the method of writing a pattern according to Embodiment 5. As shown in FIG. 25, the dose modulation rate setting process (S602), the modulated dose table creation process (S604), the data conversion process (S606), the charge amount map creation process (S608), and the maximum dose operation process (S610) are performed by the pattern writing data conversion apparatus 500. Next, a verification process (S612), a threshold Q' search process (S614), an inspection process (S616), a threshold D' search process (S622), and an inspection process (S624) are performed by the inspection apparatus 300. Next, a shot data generation process (S630), a dose operation process (S632), a correction process (S634), and a pattern writing process (S636) are performed by the lithography apparatus 100.

In Embodiment 5, the inspection apparatus 300 and the lithography apparatus 100 are separated and thus, apparatus specifications of the lithography apparatus 100 to be used are not available when the amount of electric charge Q and the maximum dose Dmax are inspected by the inspection apparatus 300. Thus, in Embodiment 5, an inquiry is made about whether the lithography apparatus 100 to be used is the scheduled apparatus.

First, in the threshold Q' search process (S614), the search unit 661 reads process parameters and apparatus specifications from the storage apparatus 648 storing process parameters to search for the charge amount threshold Q' indicating the maximum amount of electric charge that can be used for such process parameters and apparatus specifications by referring to the charge amount threshold Q' database stored in the storage apparatus 646.

Similarly, in the threshold D' search process (S622), the search unit 663 reads process parameters and apparatus specifications from the storage apparatus 648 storing process parameters to search for the maximum dose threshold D' indicating the maximum dose that can be used for such process parameters and apparatus specifications by referring to the maximum dose threshold D' database stored in the storage apparatus 646.

In the verification process (S612), on the other hand, the inquiry unit 665 makes an inquiry about whether the apparatus specifications input from the storage apparatus 648 match those of the lithography apparatus 100 to be used this time. More specifically, the inquiry unit 665 outputs the apparatus specifications input from the storage apparatus 648 to the verification unit 667 in the lithography apparatus 100. Then, in the lithography apparatus 100, the verification unit 667 verifies whether information of the apparatus specifications input from the inspection apparatus 300 and information of the apparatus specifications stored in the storage apparatus 649 match. If both pieces of information match, OK data is returned to the inspection apparatus 300. If both pieces of information do not match, error information is output as rejected.

If the verification of the apparatus specifications is NG, pattern writing is stopped. Alternatively, after information of the apparatus specifications being input from the lithography apparatus 100, the search unit 661 may search for the charge amount threshold Q' indicating the maximum amount of electric charge that can be used for such process parameters and the apparatus specifications from the lithography apparatus 100 by referring to the charge amount threshold Q' database. Similarly, after information of the apparatus specifications being input from the lithography apparatus 100, the search unit 663 may search for the maximum dose threshold D' indicating the maximum dose that can be used for such process parameters and the apparatus specifications from the lithography apparatus 100 by referring to the charge amount threshold Q' database.

The respective contents of the inspection process performed by the charge amount inspection unit 660 and the dose inspection unit 662 are the same as those in Embodiment 4.

As has been described above, the inspection function may suitably be separated from the lithography apparatus 100.

Embodiment 6

In Embodiments 4, 5, the dose is corrected by using the modulated dose rate, but the dose correction is not limited to such examples. In Embodiment 6, a case when the dose itself used for irradiation of each figure is preset will be described.

Figure 26:
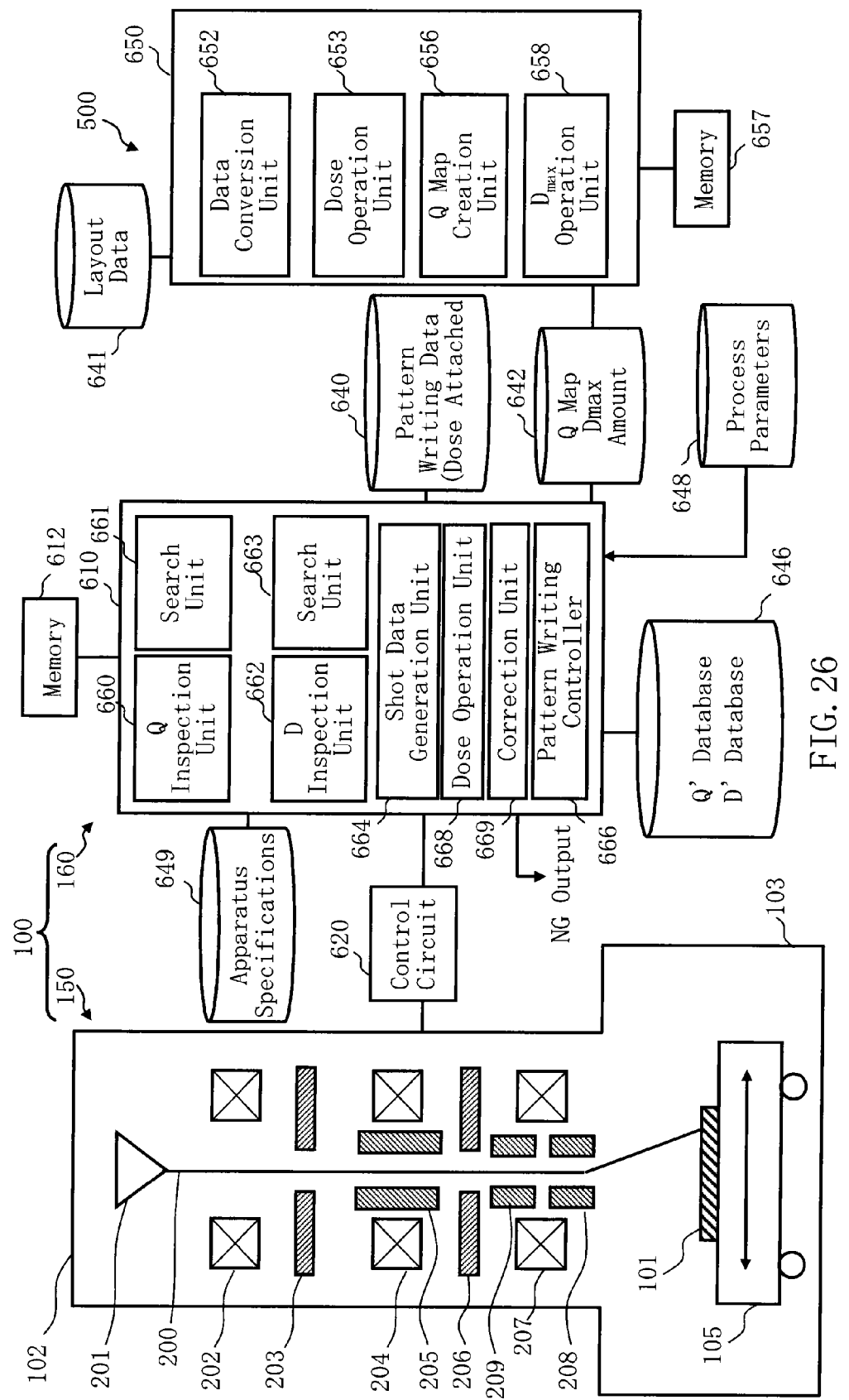
FIG. 26 is a conceptual diagram showing the configuration of the pattern writing system according to Embodiment 6.

FIG. 26 is a conceptual diagram showing the configuration of the pattern writing system according to Embodiment 6. FIG. 26 is the same as FIG. 22 except that instead of the dose modulation rate setting unit 651 and the modulated dose table creation unit 654, a dose operation unit 653 is arranged and the storage apparatus 644 and the correction unit 669 are deleted. In pattern writing data stored in the storage apparatus 640, the dose is defined for each figure as additional data. The contents not specifically described below are the same as those in Embodiment 4. The flow chart showing principal processes of the method of writing a pattern according to Embodiment 6 is the same as in FIG. 23 except that instead of the dose modulation rate setting process (S602) and the modulated dose table creation process (S604), a dose operation process is added and thus, the description thereof is omitted.

First, as the dose operation process, the dose operation unit 653 in the pattern writing data conversion apparatus 500 operates the dose for each of a plurality of figures defined for layout data. The operation of the dose may be optimized based on past track record data or simulations.

Then, in the pattern writing data generated by the data conversion unit 652, instead of the index number (identifier) to identify the modulated dose rate (modulation rate) shown in FIG. 3, the dose is added to each figure as additional data. Alternatively, figures for which the dose is defined and figures for which no dose is defined may be mixed. In the case in which both types of figures are mixed, a predetermined dose is used for figures for which no dose is defined. For example, the base doses of the beam may be used.

The charge amount map creation unit 656 divides an arrangement region of the layout data 10 into mesh regions of a predetermined size. Then, the charge amount map creation unit 656 operates the amount of electric charge Q stored in the mesh region of coordinates (i, j) by irradiation of an electron beam for each mesh region. Then, the charge amount map creation unit 656 creates an electric charge amount map summarizing the amount of electric charge Q in each mesh region. The amount of electric charge Q in each mesh region may be calculated by operating a value obtained by multiplying the area $M_{(i,j)}$ of the figure by the dose operated for the figure for each figure in the mesh region and adding up an operation result of each figure in the mesh region. The electric charge amount map is created as described above and stored in the storage apparatus 642.

The maximum dose operation unit 658 operates, among operated doses, the maximum dose Dmax. The value of the maximum dose Dmax is stored in the storage apparatus 642.

Hereinafter, the inspection method of the amount of electric charge and the maximum dose in the lithography apparatus is the same as in Embodiment 4.

As the dose operation process, the dose operation unit 668 operates the dose d for each mesh region in a predetermined size. The dose defined for each figure as a base of shot figures may be used as the dose d for each shot figure.

Even if the dose is defined as additional data for each figure in pattern writing data as described above, beam irradiation of an abnormal dose due to the pattern writing data input into a lithography apparatus can be avoided. As a result, abnormal pattern dimensions CD, resist evaporation, and lithography apparatus contamination (or a lithography apparatus failure) caused by beam irradiation of an abnormal dose can be avoided.

Embodiment 7

In Embodiment 6, the amount of electric charge and the maximum does are inspected in the lithography apparatus 100, but the inspection is not limited to the lithography apparatus 100. In Embodiment 7, a case in which a function unit that performs an inspection process is arranged off-line and configured as an inspection apparatus separately from the lithography apparatus 100 will be described.

Figure 27:
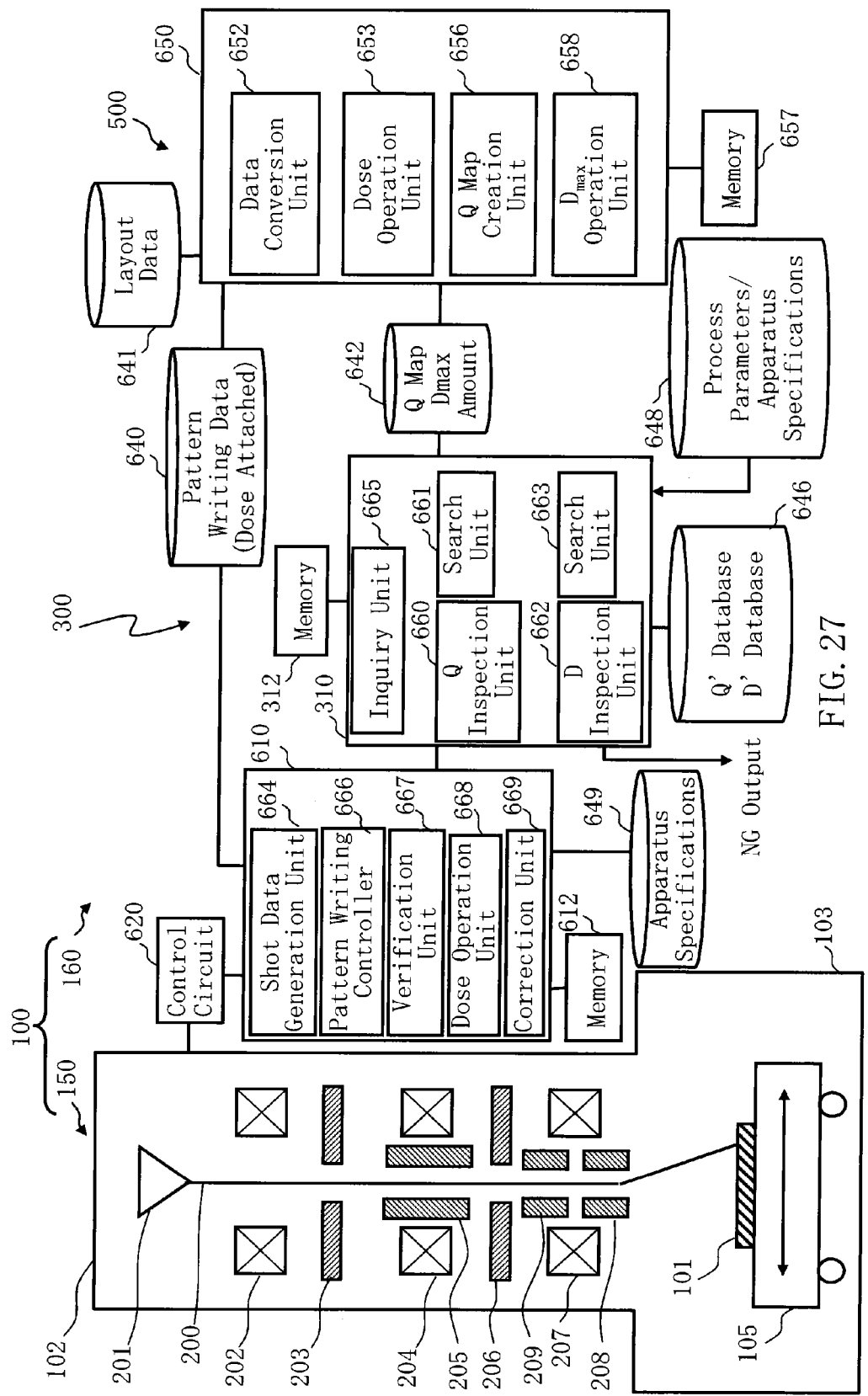
FIG. 27 is a conceptual diagram showing the configuration of the pattern writing system according to Embodiment 7.
Figure 28:
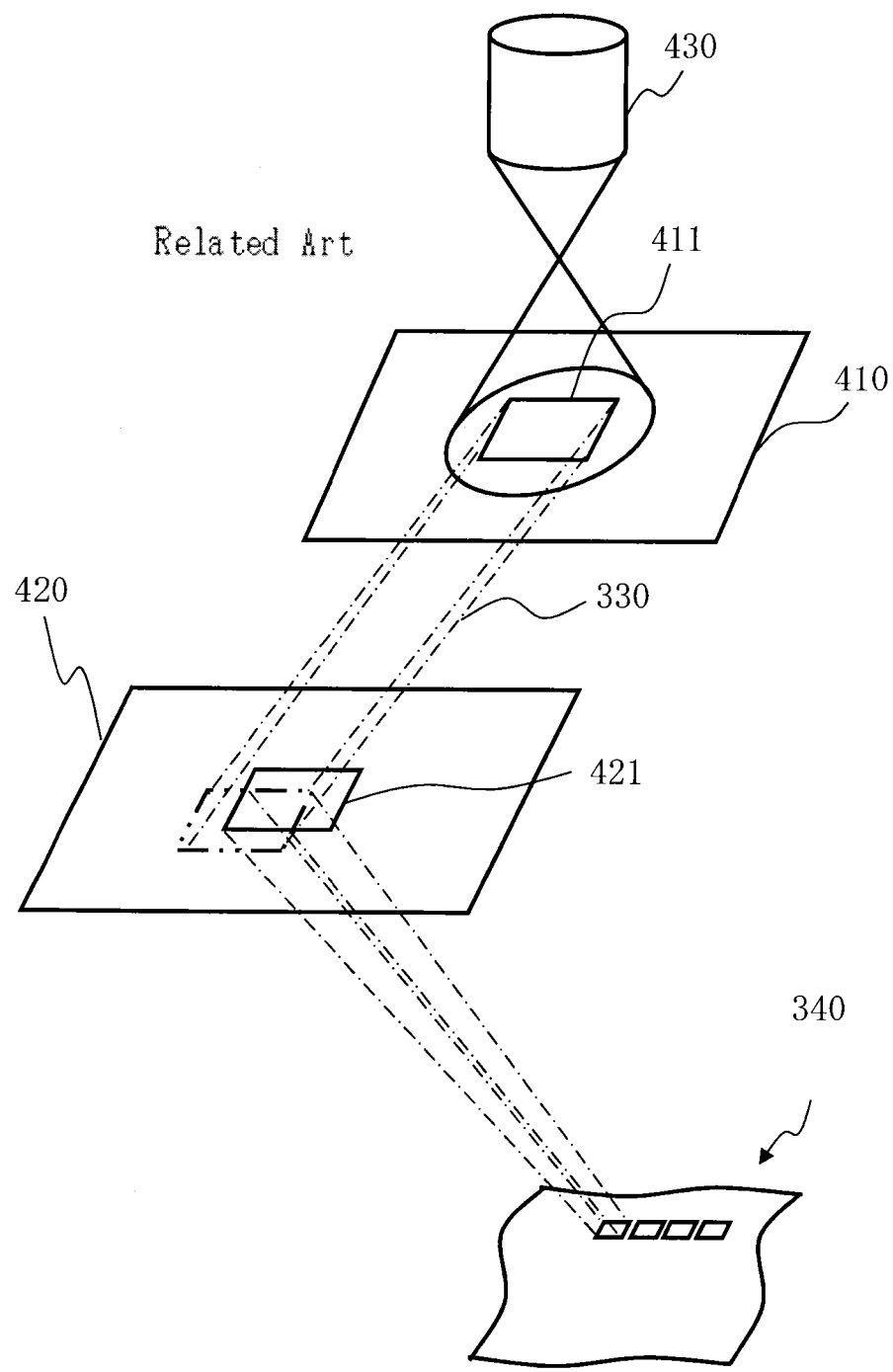
FIG. 28 is a conceptual diagram for explaining an operation of a variable-shaped electron beam lithography apparatus.

FIG. 27 is a conceptual diagram showing the configuration of the pattern writing system according to Embodiment 7. In FIG. 27, the pattern writing system includes the lithography apparatus 100, the inspection apparatus 300, and the pattern writing data conversion apparatus 500. In addition, a parameter information creation tool and the like (not shown) may also be included. In FIG. 27, the inspection apparatus 300 includes the control computer 310 and the memory 312. Also, the storage apparatuses 642, 646 are changed from the configuration of the lithography apparatus 100 to the configuration of the inspection apparatus 300. In addition, the charge amount inspection unit 660, the search units 661, 663, and the dose inspection unit 662 are changed from the configuration of the lithography apparatus 100 to the configuration of the inspection apparatus 300. Thus, the charge amount inspection unit 660, the search units 661, 663, and the dose inspection unit 662 are arranged in the control computer 310. Further, the inquiry unit 665 is arranged in the control computer 310. The function such as the charge amount inspection unit 660, the search units 661, 663, the dose inspection unit 662, and the inquiry unit 665 may be configured by hardware such as an electric circuit or by software such as a program executing these functions. Alternatively, the function may be configured by a combination of hardware and software. Information input into or output from the charge amount inspection unit 660, the search units 661, 663, the dose inspection unit 662, and the inquiry unit 665 and information during operation are stored in the memory 312 each time.

Further, the verification unit 667 is arranged in the control computer 610. The function such as the shot data generation unit 664, the pattern writing controller 666, the verification unit 667, and the dose operation unit 668 may be configured by hardware such as an electric circuit or by software such as a program executing these functions. Alternatively, the function may be configured by a combination of hardware and software. Information input into or output from the shot data generation unit 664, the pattern writing controller 666, the verification unit 667, and the dose operation unit 668 and information during operation are stored in the memory 612 each time.

In FIG. 27, the other configuration is the same as in FIG. 26. The contents not specifically described below are the same as those in Embodiment 6. The flowchart showing principal processes of the method of writing a pattern according to Embodiment 7 is the same as in FIG. 25 except that instead of the dose modulation rate setting process (S602) and the modulated dose table creation process (S604), the dose operation process is added and thus, the description thereof is omitted.

In Embodiment 7, the inspection apparatus 300 and the lithography apparatus 100 are separated and thus, apparatus specifications of the lithography apparatus 100 to be use are not available when the amount of electric charge Q and the maximum dose Dmax are inspected by the inspection apparatus 300. Thus, in Embodiment 7, like in Embodiment 5, an inquiry is made about whether the lithography apparatus 100 to be used is the scheduled apparatus. The method of making an inquiry about apparatus specifications is the same as in Embodiment 5.

In the foregoing, the embodiments have been described with reference to concrete examples. However, the present invention is not limited to such concrete examples.

Parts of the apparatus configuration, the control method, and the like which are not needed to be explained directly for the explanation of the present invention are not described. However, a necessary apparatus configuration and a necessary control method can be appropriately selected and used.

For example, a control unit configuration which controls the lithography apparatus 100 is not described. However, a necessary control unit configuration is appropriately selected and used, as a matter of course.

In addition, all charged particle beam lithography apparatuses and pattern writing methods which include the elements of the present invention and can be attained by appropriately changing in design by a person skilled in the art are included in the spirit and scope of the invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An inspection method of pattern writing data comprising:
creating an area map of a figure pattern to be written on predetermined regions of a target object by using modulation rate data to modulate a dose in a case that a plurality of figure patterns is written on the target object by using a charged particle beam, and layout data in which the plurality of figure patterns is defined, the area map being created for each modulation rate for modulating the dose;
converting the layout data into pattern writing data to be input into a lithography apparatus; and
inspecting an amount of electric charge, by using the area map, to be used when a pattern is written on the target object by using the pattern writing data, the amount being inspected for each predetermined region,
wherein the area map is created before the pattern writing data is input into the lithography apparatus and the inspecting is performed after the creation of the area map and before the pattern writing data is input into the lithography apparatus.

2. The method according to claim 1, wherein when the area map is created, the layout data is converted into the pattern writing data in parallel.

3. The method according to claim 1, wherein the plurality of figure patterns contains figure patterns to which an identifier to identify the modulation rate is defined as additional data and figure patterns for which the identifier is not defined and a predetermined modulation rate is used for the figure patterns for which the identifier is not defined.

4. The method according to claim 1, wherein the layout data contains a plurality of chip data and the modulation rate is set for each chip.

5. An inspection method of pattern writing data comprising:
converting layout data in which a plurality of figure patterns is defined into pattern writing data to be input into a lithography apparatus;
creating an electric charge amount map defining an amount of electric charge of an irradiated charged particle beam for each mesh region of a plurality of mesh regions, obtained by dividing a pattern writing region of a target object into mesh shapes, in parallel with the converting; and
inspecting whether an amount of electric charge defined in the electric charge amount map is equal to or less than a threshold for each mesh region, wherein the inspecting is performed after the creation of the electric charge amount map and before the pattern writing data is input into the lithography apparatus.

* * * * *